US007165552B2

(12) United States Patent
Deem et al.

(10) Patent No.: US 7,165,552 B2
(45) Date of Patent: *Jan. 23, 2007

(54) METHODS AND APPARATUS FOR TREATMENT OF PATENT FORAMEN OVALE

(75) Inventors: Mark E. Deem, Mountain View, CA (US); Hanson Gifford, III, Woodside, CA (US); William Malecki, San Francisco, CA (US); Kenneth Horne, Palo Alto, CA (US)

(73) Assignee: Cierra, Inc., Redwood City, CA (US)

( * ) Notice: Subject to any disclaimer, the term of this patent is extended or adjusted under 35 U.S.C. 154(b) by 289 days.

This patent is subject to a terminal disclaimer.

(21) Appl. No.: 10/665,974

(22) Filed: Sep. 18, 2003

(65) Prior Publication Data
US 2005/0034735 A1 Feb. 17, 2005

Related U.S. Application Data

(60) Provisional application No. 60/490,082, filed on Jul. 24, 2003, provisional application No. 60/478,035, filed on Jun. 11, 2003, provisional application No. 60/458,854, filed on Mar. 27, 2003.

(51) Int. Cl.
*A61B 18/18* (2006.01)
*A61B 17/08* (2006.01)
*A61B 19/00* (2006.01)

(52) U.S. Cl. .................. 128/898; 606/41; 606/213; 607/122; 607/101

(58) Field of Classification Search ............ 606/27–31, 606/41, 47–50, 213; 607/101, 102, 122; 128/898
See application file for complete search history.

(56) References Cited

U.S. PATENT DOCUMENTS 2,275,167 A  3/1942  Bierman (Continued)

FOREIGN PATENT DOCUMENTS

EP  135840 A2  4/1985

(Continued)

OTHER PUBLICATIONS

Anzola et al., "Potential Source of Cerebral Embolism in Migraine with Aura," *Neurology* (1999) 52(8): 1622.

(Continued)

*Primary Examiner*—Michael Peffley
(74) *Attorney, Agent, or Firm*—Townsend and Townsend and Crew LLP

(57) ABSTRACT

Methods and apparatus for treatment of patent foramen ovale (PFO) generally involve use of a catheter having at least one closure device at its distal end. In some embodiments, the catheter also includes one or more energy transmission members for delivering energy to the closure device(s) and to the tissue adjacent the PFO to induce closure of the PFO. Closure devices may comprise, for example, a bioresorbable matrix or a non-resorbable matrix. In some embodiments, the closure device contains particles dispersed within the closure device to increase conductance and/or to reduce resistance and/or impedance. An exemplary method involves advancing a catheter to position its distal end into the tunnel of the PFO and fixing the closure device within the tunnel of the patent foramen PFO.

14 Claims, 23 Drawing Sheets

U.S. PATENT DOCUMENTS

| | | | |
|---|---|---|---|
| 2,580,628 A | 1/1952 | Welsh |
| 2,888,928 A | 6/1959 | Seiger |
| 3,490,442 A | 1/1970 | Streu |
| 3,862,627 A | 1/1975 | Hans, Sr. |
| 3,874,388 A | 4/1975 | King et al. |
| 3,906,955 A | 9/1975 | Roberts |
| 4,307,720 A | 12/1981 | Weber, Jr. |
| 4,326,529 A | 4/1982 | Doss et al. |
| 4,473,077 A | 9/1984 | Noiles et al. |
| 4,485,817 A | 12/1984 | Swiggett |
| 4,556,065 A | 12/1985 | Hoffmann |
| 4,562,838 A | 1/1986 | Walker |
| 4,682,596 A | 7/1987 | Bales et al. |
| 4,788,975 A | 12/1988 | Shturman et al. |
| 4,798,594 A | 1/1989 | Hillstead |
| 4,832,048 A | 5/1989 | Cohen |
| 4,884,567 A | 12/1989 | Elliot et al. |
| 4,895,565 A | 1/1990 | Hillstead |
| 4,911,159 A | 3/1990 | Johnson et al. |
| 4,919,129 A | 4/1990 | Weber, Jr. et al. |
| 4,929,246 A | 5/1990 | Sinofsky |
| 4,976,711 A | 12/1990 | Parins et al. |
| 4,986,889 A | 1/1991 | Charamathieu et al. |
| 5,041,095 A | 8/1991 | Littrell |
| 5,042,707 A | 8/1991 | Taheri |
| 5,055,100 A | 10/1991 | Olsen |
| 5,056,517 A | 10/1991 | Fenici |
| 5,057,107 A | 10/1991 | Parins et al. |
| 5,071,417 A | 12/1991 | Sinofsky |
| 5,071,418 A | 12/1991 | Rosenbaum |
| 5,078,717 A | 1/1992 | Parins et al. |
| 5,099,827 A | 3/1992 | Melzer et al. |
| RE33,925 E | 5/1992 | Bales et al. |
| 5,125,928 A | 6/1992 | Parins et al. |
| 5,156,608 A | 10/1992 | Troidl et al. |
| 5,156,613 A | 10/1992 | Sawyer |
| 5,171,311 A | 12/1992 | Rydell |
| 5,195,959 A | 3/1993 | Smith |
| 5,196,007 A | 3/1993 | Ellman et al. |
| 5,197,963 A | 3/1993 | Parins |
| 5,207,670 A | 5/1993 | Sinofsky |
| 5,209,756 A | 5/1993 | Seedhom et al. |
| 5,290,278 A | 3/1994 | Anderson |
| 5,292,362 A | 3/1994 | Bass et al. |
| 5,295,955 A | 3/1994 | Rosen et al. |
| 5,300,065 A | 4/1994 | Anderson |
| 5,336,221 A | 8/1994 | Anderson |
| 5,336,252 A | 8/1994 | Cohen |
| 5,342,413 A | 8/1994 | Hirschberg et al. |
| 5,345,935 A | 9/1994 | Hirsch |
| 5,370,675 A | 12/1994 | Edwards et al. |
| 5,380,304 A | 1/1995 | Parker |
| 5,383,917 A | 1/1995 | Desai et al. |
| 5,405,322 A | 4/1995 | Lennox et al. |
| 5,409,479 A | 4/1995 | Dew et al. |
| 5,409,481 A | 4/1995 | Poppas et al. |
| 5,500,012 A | 3/1996 | Brucker et al. |
| 5,505,730 A | 4/1996 | Edwards |
| 5,507,744 A | 4/1996 | Tay et al. |
| 5,540,677 A | 7/1996 | Sinofsky |
| 5,569,239 A | 10/1996 | Sinofsky |
| 5,571,216 A | 11/1996 | Anderson |
| 5,575,772 A | 11/1996 | Lennox |
| 5,584,872 A | 12/1996 | Lafontaine et al. |
| 5,611,794 A | 3/1997 | Sauer et al. |
| 5,620,481 A | 4/1997 | Desai et al. |
| 5,626,607 A * | 5/1997 | Malecki et al. ............. 606/205 |
| 5,662,643 A | 9/1997 | Kung et al. |
| 5,665,109 A | 9/1997 | Yoon |
| 5,669,934 A | 9/1997 | Sawyer |
| 5,693,078 A | 12/1997 | Desai et al. |
| 5,709,224 A | 1/1998 | Behl et al. |
| 5,713,891 A | 2/1998 | Poppas |
| 5,725,522 A | 3/1998 | Sinofsky |
| 5,730,742 A | 3/1998 | Wojciechowicz |
| 5,749,895 A | 5/1998 | Sawyer et al. |
| 5,782,899 A | 7/1998 | Imran |
| 5,814,065 A | 9/1998 | Diaz |
| 5,824,015 A | 10/1998 | Sawyer |
| 5,827,265 A | 10/1998 | Glinsky et al. |
| 5,846,196 A | 12/1998 | Siekmeyer et al. |
| 5,855,312 A | 1/1999 | Toledano |
| 5,871,443 A | 2/1999 | Edwards et al. |
| 5,919,200 A * | 7/1999 | Stambaugh et al. ......... 606/159 |
| 5,925,078 A | 7/1999 | Anderson |
| 5,928,266 A | 7/1999 | Kontos |
| 5,931,165 A | 8/1999 | Reich et al. |
| 5,944,738 A | 8/1999 | Amplatz et al. |
| 5,972,023 A | 10/1999 | Tanner et al. |
| 5,972,024 A | 10/1999 | Northrup, III et al. |
| 6,004,316 A | 12/1999 | Laufer |
| 6,036,699 A | 3/2000 | Andreas et al. |
| 6,056,760 A | 5/2000 | Koike et al. |
| 6,063,081 A | 5/2000 | Mulier |
| 6,063,085 A | 5/2000 | Tay et al. |
| 6,083,223 A | 7/2000 | Baker |
| 6,086,570 A | 7/2000 | Aboul-Hosn et al. |
| 6,086,586 A | 7/2000 | Hooven |
| 6,087,552 A | 7/2000 | Gregory |
| 6,132,429 A | 10/2000 | Baker |
| 6,149,660 A | 11/2000 | Laufer et al. |
| 6,156,032 A | 12/2000 | Lennox |
| 6,168,594 B1 | 1/2001 | Lafontaine |
| 6,211,335 B1 | 4/2001 | Owen et al. |
| 6,221,068 B1 | 4/2001 | Fried et al. |
| 6,257,241 B1 | 7/2001 | Wampler |
| 6,290,674 B1 | 9/2001 | Roue et al. |
| 6,302,898 B1 | 10/2001 | Edwards et al. |
| 6,323,037 B1 | 11/2001 | Lauto et al. |
| 6,325,798 B1 | 12/2001 | Edwards et al. |
| 6,355,030 B1 | 3/2002 | Aldrich et al. |
| 6,383,198 B1 | 5/2002 | Hamilton |
| 6,391,048 B1 * | 5/2002 | Ginn et al. .................. 606/213 |
| 6,391,049 B1 | 5/2002 | McNally et al. |
| 6,398,779 B1 | 6/2002 | Buysee et al. |
| 6,398,782 B1 | 6/2002 | Pecor et al. |
| 6,401,720 B1 | 6/2002 | Stevens et al. |
| 6,419,669 B1 | 7/2002 | Frazier et al. |
| 6,423,057 B1 | 7/2002 | He et al. |
| 6,436,088 B2 | 8/2002 | Frazier et al. |
| 6,456,865 B2 | 9/2002 | Samson |
| 6,458,100 B2 | 10/2002 | Roue et al. |
| 6,475,213 B1 | 11/2002 | Whayne et al. |
| 6,482,224 B1 | 11/2002 | Michler et al. |
| 6,514,250 B1 | 2/2003 | Jahns et al. |
| 6,558,314 B1 | 5/2003 | Adelman et al. |
| 6,562,037 B2 | 5/2003 | Paton et al. |
| 6,583,117 B2 | 6/2003 | Owen et al. |
| 6,584,360 B2 | 6/2003 | Francischelli et al. |
| 6,589,237 B2 | 7/2003 | Woloszko |
| 6,606,523 B1 | 8/2003 | Jenkins |
| 6,641,604 B1 | 11/2003 | Adelman |
| 6,645,202 B1 | 11/2003 | Pless et al. |
| 6,645,225 B1 | 11/2003 | Atkinson |
| 6,648,897 B2 | 11/2003 | Hamilton |
| 6,652,518 B2 | 11/2003 | Wellman |
| 6,669,693 B2 | 12/2003 | Friedman |
| 6,676,685 B2 | 1/2004 | Pedros et al. |
| 6,682,546 B2 | 1/2004 | Amplatz |
| 6,702,835 B2 | 3/2004 | Ginn |
| 6,712,804 B2 | 3/2004 | Roue et al. |
| 6,712,836 B1 | 3/2004 | Berg et al. |
| 6,716,211 B2 | 4/2004 | Mulier et al. |
| 6,726,718 B1 | 4/2004 | Carlyle et al. |

| | | |
|---|---|---|
| 6,730,108 B2 | 5/2004 | Van Tassel et al. |
| 6,733,498 B2 | 5/2004 | Paton et al. |
| 6,736,810 B2 | 5/2004 | Hoey et al. |
| 6,755,790 B2 | 6/2004 | Stewart et al. |
| 6,770,072 B1 | 8/2004 | Truckai et al. |
| 6,776,784 B2 | 8/2004 | Ginn |
| 6,790,218 B2 | 9/2004 | Jayaraman |
| 6,846,319 B2 | 1/2005 | Ginn et al. |
| 6,887,238 B2 | 5/2005 | Jahns |
| 6,893,431 B2 | 5/2005 | Naimark et al. |
| 6,926,716 B2 | 8/2005 | Baker et al. |
| 6,929,644 B2 | 8/2005 | Truckai et al. |
| 6,946,134 B1 | 9/2005 | Rosen et al. |
| 2001/0037129 A1 | 11/2001 | Thill |
| 2001/0051803 A1 | 12/2001 | Desai et al. |
| 2002/0128672 A1 | 9/2002 | Dinger et al. |
| 2002/0143322 A1 | 10/2002 | Haghighi |
| 2003/0028189 A1 | 2/2003 | Woloszko et al. |
| 2003/0045893 A1 | 3/2003 | Ginn |
| 2003/0045901 A1* | 3/2003 | Opolski ............... 606/213 |
| 2003/0050665 A1 | 3/2003 | Ginn |
| 2003/0065364 A1 | 4/2003 | Wellman et al. |
| 2003/0069570 A1 | 4/2003 | Witzel |
| 2003/0078578 A1 | 4/2003 | Truckai et al. |
| 2003/0093071 A1 | 5/2003 | Hauck et al. |
| 2003/0120268 A1 | 6/2003 | Bertolero et al. |
| 2003/0144652 A1 | 7/2003 | Baker et al. |
| 2003/0144694 A1* | 7/2003 | Chanduszko et al. ....... 606/213 |
| 2003/0158551 A1 | 8/2003 | Paton et al. |
| 2003/0199868 A1 | 10/2003 | Desai et al. |
| 2003/0208232 A1 | 11/2003 | Blaeser et al. |
| 2003/0225421 A1 | 12/2003 | Peavey et al. |
| 2003/0233091 A1 | 12/2003 | Whayne et al. |
| 2004/0059347 A1 | 3/2004 | Hamilton |
| 2004/0092973 A1 | 5/2004 | Chanduszko et al. |
| 2004/0098031 A1 | 5/2004 | Van der Burg et al. |
| 2004/0098042 A1 | 5/2004 | Devellian et al. |
| 2004/0102721 A1 | 5/2004 | Mckinley |
| 2004/0143292 A1 | 7/2004 | Marino et al. |
| 2004/0153057 A1 | 8/2004 | Davison |
| 2004/0153098 A1 | 8/2004 | Chin et al. |
| 2004/0176799 A1 | 9/2004 | Chanduszko et al. |
| 2004/0220596 A1 | 11/2004 | Frazler et al. |
| 2004/0243122 A1* | 12/2004 | Auth et al. ............ 606/41 |
| 2004/0249398 A1 | 12/2004 | Ginn |
| 2005/0021059 A1 | 1/2005 | Cole et al. |
| 2005/0033288 A1 | 2/2005 | Auth et al. |
| 2005/0033327 A1 | 2/2005 | Gainor et al. |
| 2005/0055050 A1 | 3/2005 | Alfaro |
| 2005/0065506 A1 | 3/2005 | Phan |
| 2005/0065509 A1 | 3/2005 | Coldwell et al. |
| 2005/0070923 A1 | 3/2005 | Mcintosh |
| 2005/0075665 A1 | 4/2005 | Brenzel et al. |
| 2005/0119675 A1 | 6/2005 | Adams et al. |
| 2005/0125032 A1 | 6/2005 | Whisenant et al. |
| 2005/0171526 A1 | 8/2005 | Rioux et al. |
| 2005/0187568 A1 | 8/2005 | Klenk et al. |
| 2005/0192626 A1 | 9/2005 | Widomski et al. |
| 2005/0192627 A1 | 9/2005 | Whisenant et al. |
| 2005/0192654 A1 | 9/2005 | Chanduszko et al. |
| 2005/0209636 A1 | 9/2005 | Widomski et al. |
| 2005/0216054 A1 | 9/2005 | Widomski et al. |
| 2005/0251201 A1 | 11/2005 | Roue et al. |
| 2005/0256532 A1 | 11/2005 | Nayak et al. |
| 2005/0267495 A1 | 12/2005 | Ginn et al. |
| 2005/0267525 A1 | 12/2005 | Chanduszko |
| 2006/0036284 A1 | 2/2006 | Blaeser et al. |

FOREIGN PATENT DOCUMENTS

| | | |
|---|---|---|
| EP | 199694 A2 | 10/1986 |
| EP | 0265532 A1 | 5/1988 |
| EP | 0375556 A1 | 6/1990 |
| EP | 0428812 A1 | 5/1991 |
| EP | 0947165 A1 | 10/1999 |
| GB | 1260919 | 1/1972 |
| GB | 1550676 | 8/1979 |
| GB | 2 359 024 A | 8/2001 |
| WO | WO 85/00018 A1 | 1/1985 |
| WO | WO 87/04081 A1 | 7/1987 |
| WO | WO 90/04352 A1 | 5/1990 |
| WO | WO 91/15996 A1 | 10/1991 |
| WO | WO 92/04864 A1 | 4/1992 |
| WO | WO 93/05705 A1 | 4/1993 |
| WO | WO 93/15791 A1 | 8/1993 |
| WO | WO 94/00178 A1 | 1/1994 |
| WO | WO 98/07375 A1 | 2/1998 |
| WO | WO 99/18862 A1 | 4/1999 |
| WO | WO 99/18864 A1 | 4/1999 |
| WO | WO 99/18870 A1 | 4/1999 |
| WO | WO 99/18871 A1 | 4/1999 |
| WO | WO 99/23959 | 5/1999 |
| WO | WO 00/07506 A2 | 2/2000 |
| WO | WO 00/09027 A1 | 2/2000 |
| WO | WO 01/013810 | 3/2001 |
| WO | WO 01/78596 A1 | 10/2001 |
| WO | WO 03/022159 A1 | 3/2003 |
| WO | WO 03/022160 A1 | 3/2003 |
| WO | WO 03/026496 A2 | 4/2003 |
| WO | WO 03/053493 | 7/2003 |
| WO | WO 03/071957 A2 | 9/2003 |
| WO | WO 03/082076 A2 | 10/2003 |
| WO | WO 03/094742 A1 | 11/2003 |
| WO | WO 2004/019791 A2 | 3/2004 |
| WO | WO 04/043266 A2 | 5/2004 |
| WO | WO 04/069055 A2 | 8/2004 |
| WO | WO 2004/082532 A1 | 9/2004 |
| WO | WO 2004/091411 A2 | 10/2004 |
| WO | WO 2005/006990 A2 | 1/2005 |
| WO | WO 2005/027753 A1 | 3/2005 |
| WO | WO 2005/034738 A2 | 4/2005 |
| WO | WO 2005/046487 | 5/2005 |
| WO | WO 2005/074814 | 8/2005 |
| WO | WO 2005/115256 | 12/2005 |

OTHER PUBLICATIONS

De Castro et al., "Morphological and Functional Characteristics of Patent Foramen Ovale and Their Embolic Implications," *Stroke* (Oct. 2002), pp. 2407-2413.

Cordis Corporation, Cordis Ducor® Lumeleo® Electorode Catheters [brochure], Cordis Corporation, (Dec. 1984), 2 pages.

Del Sette, "Migraine with Aura and Right-to-Left Shunt on Transcranial Doppler: A Case Control Study," *Cerebrovas Dis* (1998) 8:327-330.

Gillette, "Catheter Ablation in Dysrhythmias," *Cardio*, (Mar. 1984), pp. 67-69.

Ho et al., "Morphological Features Pertinent to Interventional Closure of Patent Oval Foramen," *J Interventional Cardiology*, vol. 16 No. 1, (2003), pp. 33-34.

Kennedy et al., "High-burst-Strength, feedback-controlled bipolar vessel sealing," *Surg Endosc* (1998) 12:876-878.

Koenig et al., "Role of Intracardiac Echocardiographic Guidance in Transcatheter Closure of Atrial Septal Defects and Patent Foramen Ovale Using the Amplatzer® Device," *J. Interventional Cardiology*, (2003) 16(1): 51-62.

Morady, "Transvenous Catheter Ablation of a Posterospetial Accessory Pathway in a Patient with the Wolff Parkinson-White Syndrome," *The New England Journal of Medicine*, (Mar. 15, 1984), 310(11): 705-707.

Morandi et al., "Transcatheter Closure of Patent Foramen Ovale: A New Migraine Treatment?" *J Interventional Cardiology*, (2003), 16(1): 39-42.

Pfleger, "Haemodynamic Quantification of Different Provocation Manoeuvres by Simultaneous Measurement of Right and Left Atrial Pressure: Implications for the Echocardiographic Detection of Persistent Foramen Ovale," *Eur J Echocardiography* (2001) 2:88-93.

Polgar et al., "A New Technique for Closed-Chest Human His Bundle Ablation Using Suction Electrode Catheter and DC Shock," In: Perez Gomez F, ed. *Cardiac Pacing Electrophysiology Tachyarrhythmias*. Madrid, Spain: Grouz Publishers; 1985:1582-1586.

Polgar et al., "Comparison of Two Different Techniques for Closed-Chest His Bundle Ablation," In: Perez Gomez F, ed. Cardiac Pacing Electrophysiology Tachyarrhythmias. Madrid, Spain: Grouz Publishers; 1985:1578-1587.

Polgar, "Closed Chested Ablation of His Bundle: A New Technique Using Suction Electorde Catheter and DC Shock," *Nachdruck Aus: Cardio Pacing*, (1983), pp. 883-890.

Stuart, "What's All the Flap About PFO Closure?," *Start-Up: Windhover's Review of Emerging Medical Ventures*, (Nov. 10, 2004), pp. 9-14.

Sztajzel et al., "Patent Foramen Ovale, a Possible Cause of Symptomatic Migraine: A Study of 74 Patients with Acute Ischemic Stroke," *Cerebrovas Dis* (2002) 13: 102-106.

Thomas, "Patent Foramen Ovale with Right-to-left Shunting: Echocariographic Alternatives," *Eur J Echocariography* (2001) 2:74-75.

Wilmhurst et al., "Effect on Migraine of Closure of Cardiac Right-to-Left Shunts to Prevent Recurrence of Decompression Illness of Illness or Stroke or for Haemodynamic Reasons," *The Lancet*, vol. 356, (Nov. 11, 2000), pp. 1648-1651.

Wilmhurst et al., "Relationship between Migraine and Cardiac and Pulmonary Right to Left Shunts," *Clinical Science* (2001) 100:215-220.

Athiraman et al., "Selective Photothermal Tissue Interaction Using 805-nm Laser and Indocyanine Green in Tissue Welding," *Journal of X-Ray Science and Technology*, vol. 12, No. 2, (2004), pp. 117-126.

Fenner et al., "Shear Strength of Tissue Bonds as a Function of Bonding Temperature: A Proposed Mechanism for Laser-Assisted Tissue Welding," *Lasers in Medical Science*, vol. 7, (1992), pp. 39-43.

Godlewski et al., "Applications and Mechanisms of Laser Tissue Welding in 1995: Review," *Proc. SPIE*, vol. 2623, (Jan. 1996) pp. 334-341.

Olson et al., "Developing An Animal Model for the Study of Fusion Using RF Energy," *Proc. SPIE*, vol. 5312, (2004), pp. 147-161.

Ott et al., "Comparative in Vitro Study of Tissue Welding Using a 808 nm Diode Laser and a Ho:YAG laser," *Lasers Med Sci*, vol. 16, (2001) pp. 260-266.

Poppas et al., "Temperature-Controlled Laser Photocoagulation of Soft Tissue: In Vivo Evaluation Using a Tissue Welding Model," Lasers Surg Med., vol. 18, No. 4, (1996), pp. 335-344.

Stewart et al., "Laser Assisted Vascular Welding with Real Time Temperature Control," Lasers Surg Med., vol. 19, No. 1, (1996), pp. 9-16.

Tang et al., "Quantitative Changes in Collagen Levels Following 830-nm Diode Laser Welding," Lasers Surg Med., vol. 22, No. 4, (1998), pp. 207-211.

Tang et al, "Morphologic Changes in Collagen Fibers after 830 nm Diode Laser Welding," Lasers Surg Med., vol. 21, No. 5 (1997), pp. 438-443.

* cited by examiner

METHODS AND APPARATUS FOR TREATMENT OF PATENT FORAMEN OVALE

CROSS-REFERENCES TO RELATED APPLICATIONS

This application claims priority to U.S. Provisional Patent Application Nos. 60/458,854, filed on Mar. 27, 2003; 60/478,035, filed on Jun. 11, 2003, and 60/490,082, filed on Jul. 24, 2003, the full disclosures of which are incorporated herein by reference.

BACKGROUND OF THE INVENTION

The invention generally relates to medical apparatus and methods. More specifically, the invention relates to apparatus and methods for treatment of patent foramen ovale.

Fetal blood circulation is much different than adult circulation. Because fetal blood is oxygenated by the placenta, rather than the fetal lungs, blood is generally shunted away from the lungs to the peripheral tissues through a number of vessels and foramens that remain patent (i.e., open) during fetal life and typically close shortly after birth. For example, fetal blood passes directly from the right atrium through the foramen ovale into the left atrium, and a portion of blood circulating through the pulmonary artery trunk passes through the ductus arteriosus to the aorta. This fetal circulation is shown in attached FIG. 1.

At birth, as a newborn begins breathing, blood pressure in the left atrium rises above the pressure in the right atrium. In most newborns, a flap of tissue closes the foramen ovale and heals together. In approximately 20,000 babies born each year in the US, the flap of tissue is missing, and the hole remains open as an atrial septal defect (ASD). In a much more significant percentage of the population (estimates range from 5% to 20% of the entire population), the flap is present but does not heal together. This condition is known as a patent foramen ovale (PFO). Whenever the pressure in the right atrium rises above that in the left atrium, blood pressure can push this patent channel open, allowing blood to flow from the right atrium to the left atrium.

Patent foramen ovale has long been considered a relatively benign condition, since it typically has little effect on the body's circulation. More recently, however, it has been found that a significant number of strokes may be caused at least in part by PFO. In some cases, stroke may occur because a PFO allows blood containing small thrombi to flow directly from the venous circulation to the arterial circulation and into the brain, rather than flowing to the lungs where the thrombi can become trapped and gradually dissolved. In other cases, thrombi might form in the patent channel of the PFO itself and become dislodged when the pressures cause blood to flow from the right atrium to the left atrium. It has been estimated that patients with PFOs who have already had cryptogenic strokes have a 4% risk per year of having another stroke.

Further research is currently being conducted into the link between PFO and stroke. At the present time, if someone with a PFO has two or more strokes, the healthcare system in the U.S. may reimburse a surgical or other interventional procedure to definitively close the PFO. It is likely, however, that a more prophylactic approach would be warranted to close PFOs to prevent the prospective occurrence of a stroke. The cost and potential side-effects and complications of such a procedure must be low, however, since the event rate due to PFOs is relatively low. In younger patients, for example, PFOs sometimes close by themselves over time without any adverse health effects.

Another highly prevalent and debilitating condition—chronic migraine headaches—has also been linked with PFO. Although the exact link has not yet been explained, PFO closure has been shown to eliminate or significantly reduce migraine headaches in many patients. Again, prophylactic PFO closure to treat chronic migraine headaches might be warranted if a relatively non-invasive procedure were available.

Currently available interventional therapies for PFO are generally fairly invasive and/or have potential drawbacks. One strategy is simply to close a PFO during open heart surgery for another purpose, such as heart valve surgery. This can typically be achieved via a simple procedure such as placing a stitch or two across the PFO with vascular suture. Performing open heart surgery purely to close an asymptomatic PFO or even a very small ASD, however, would be very hard to justify.

A number of interventional devices for closing PFOs percutaneously have also been proposed and developed. Most of these devices are the same as or similar to ASD closure devices. They are typically "clamshell" or "double umbrella" shaped devices which deploy an area of biocompatible metal mesh or fabric (ePTFE or Dacron, for example) on each side of the atrial septum, held together with a central axial element, to cover the PFO. This umbrella then heals into the atrial septum, with the healing response forming a uniform layer of tissue or "pannus" over the device. Such devices have been developed, for example, by companies such as Nitinol Medical Technologies, Inc. (Boston, Mass.) and AGA Medical, Inc. (White Bear Lake, Minn.). U.S. Pat. No. 6,401,720 describes a method and apparatus for thoracoscopic intracardiac procedures which may be used for treatment of PFO.

Although available devices may work well in some cases, they also face a number of challenges. Relatively frequent causes of complications include, for example, improper deployment, device embolization into the circulation and device breakage. In some instances, a deployed device does not heal into the septal wall completely, leaving an exposed tissue which may itself be a nidus for thrombus formation. Furthermore, currently available devices are generally complex and expensive to manufacture, making their use for prophylactic treatment of PFO impractical. Additionally, currently available devices typically close a PFO by placing material on either side of the tunnel of the PFO, compressing and opening the tunnel acutely, until blood clots on the devices and causes flow to stop. No presently known methods or devices close a PFO by inserting a device primarily into the tunnel of the PFO to cause closure.

Research into methods and compositions for tissue welding has been underway for many years. Of particular interest are technologies developed by McNally et. al., (as shown in U.S. Pat. No. 6,391,049 and Fusion Medical (as shown in U.S. Pat. Nos. 5,156,613, 5,669,934, 5,824,015 and 5,931,165). These technologies all disclose the use of energy delivery to tissue solders and patches in order to join tissue and form anastamoses between arteries, bowel, nerves, etc. Also of interest are a number of patents by inventor Sinofsky, relating to laser suturing of biological materials (e.g., U.S. Pat. Nos. 5,725,522, 5,569,239, 5,540,677 and 5,071,417). Other references, such as PCT Patent Application Publication No. WO 03/0534493, describe devices for closing PFOs involving bioresorbable materials. While these basic technologies may be applicable to the closure of PFOs, however, none of them show methods or apparatus suitable for positioning the tissues of the PFO for welding or for delivering the energy to the site to be welded.

Therefore, it would be advantageous to have improved methods and apparatus for treating a PFO. Ideally, such methods and apparatus would help seal the PFO while leaving only a harmless repair material, or possibly very little or no foreign material, in the body. Also ideally, such methods and apparatus would be relatively simple to manufacture and use, thus rendering prophylactic treatment of PFO, such as for stroke prevention, a viable option. It would also be advantageous to have a device which could effect closure of a PFO without requiring insertion of a catheter through the PFO. At least some of these objectives will be met by the present invention.

BRIEF SUMMARY OF THE INVENTION

Methods and apparatus for treatment of patent foramen ovale (PFO) generally involve use of a catheter having treatment apparatus at its distal end. In the present embodiments, the treatment apparatus includes at least one conductive element disposed at the distal end of the catheter. The treatment apparatus may also include a positive stop feature to limit the penetration of the treatment apparatus to a predetermined depth into the PFO. The apparatus also includes an energy source, such as a radiofrequency generator, used in conjunction with a closure device.

Methods generally involve advancing the catheter to position its distal end near the PFO and using the treatment apparatus to secure a closure device to the tissue with energy and/or tissue solder or tissue adhesive to close the PFO. The closure device may be a plug that physically covers the PFO. Alternatively, the closure device may be a plug inserted selectively into the PFO.

In one aspect, a method of treating a patent foramen ovale comprises: advancing a catheter device having a proximal end, a distal end and at least one conductive element and closure device near the distal end through vasculature of a patient to position the distal end adjacent the patent foramen ovale; advancing the at least one conductive element and closure device to or into the patent foramen ovale; exposing the at least one conductive element to the closure element and/or to the tissue; and applying energy to the tissue and/or closure device to fix the device to or into the tissue of the PFO. In some embodiments, advancing the catheter comprises advancing through at least one of a femoral vein, an iliac vein, an inferior vena cava, a brachial vein, an axial vein, a subclavian vein, and a superior vena cava of the patient. In some embodiments, advancing the catheter comprises advancing over a guidewire.

In other aspects, exposing the at least one conductive element and closure device involves retracting a catheter body of the catheter to expose the at least one conductive element and closure device out of an opening in the catheter body at or near the distal end of the catheter. Alternatively, exposing the at least one conductive element and closure device may involve advancing the conductive element and closure device relative to the catheter body. In any embodiment, the at least one conductive element and closure device may be retracted and advanced as many times as desired. Optionally, any embodiment may include visualization of the PFO and/or tissue surrounding the PFO using one or more visualization devices.

In further aspects, advancing the at least one conductive element and closure device to or into the PFO optionally includes inserting at least a portion of the at least one conductive element and closure device into the PFO until a positive stop provided on the treatment apparatus engages the peripheral limits of the PFO, limiting penetration depth of the at least one conductive element and closure device.

A further aspect of advancing the closure device to or into the PFO includes providing a closure device made from a self-expanding bioresorbable, doped matrix and allowing the self expanding material of the closure device to fill and/or span the PFO. In alternative embodiments, a self-expanding or expandable matrix that is not bioresorbable may be used.

In another method of therapy, advancing the treatment apparatus comprises advancing two or more conductive elements to the PFO and using the two or more conductive elements to apply lateral, dilatory or a combination of both forces to bring the tissue of the septum primum and septum secundum of the PFO into apposition. Alternatively, the lateral and/or dilatory forces may bring the tissue of the septum primum and septum secundum into apposition with one or more of the conductive elements, or into apposition with the closure device. In this method, advancing the closure device comprises spanning the area between the two or more conductive elements with the closure device. In a further aspect of the method, advancing the closure device may comprise allowing the closure device to self-expand in and/or near the PFO to fill any space left after the primum and secundum are brought into apposition by the two or more conductive elements. In some embodiments, applying lateral, dilatory or a combination of forces may be achieved by inflating a balloon within the conductive elements, or by incorporating the conductive elements into a balloon.

Methods for fixing the closure device to the PFO include applying energy to the at least one conductive element of the treatment apparatus via the delivery catheter. In one method, monopolar radiofrequency energy is applied through the at least one conductive element and the conductively doped closure device, heating the tissue and/or closure device, to fix the closure device to the tissue and close the PFO. Alternatively, applying energy to the closure device may cause solder or adhesive-filled compartments within the closure device to rupture, fixing the closure device to the PFO.

An alternative method includes applying bipolar radiofrequency energy between the at least one conductive element and a ground electrode on the delivery catheter or proximal treatment apparatus to heat the tissue and/or closure device to fix the closure device to the tissue and close the PFO.

A further method entails applying bipolar radiofrequency energy between the two or more conductive elements of the treatment apparatus to heat the tissue and/or closure device to fix the closure device to the tissue and close the PFO. In some methods, the energy may be conducted from each of the two or more conductive elements of the treatment apparatus into specifically defined conductive pathways of the closure device.

In yet another aspect, apparatus for treating PFO comprises an elongate catheter body having a proximal end and a distal end and a treatment apparatus comprised of at least one retractable conductive element movable between a retracted position wherein the conductive element resides wholly within the catheter body and a deployed position wherein at least a portion of the conductive element extends through an opening in the catheter body adjacent the distal end. In some embodiments, the catheter body is passable over a guidewire. Also in some embodiments, the at least one retractable conductive element contains at least one positive stop provided to engage the peripheral limits of the PFO, limiting penetration depth of the at least one conductive element and closure device. Optionally, the at least one retractable conductive element comprises multiple conductive elements. Also in some embodiments, the at least one retractable conductive element is movable relative to the catheter body to extend the at least one conductive element through the PFO and retract the conductive element back through the foramen ovale.

Apparatus for treating a PFO also consist of a closure device, which may include a bioabsorbable or non-resorbable matrix. The matrix may include conductive elements to reduce impedance over the desired energy transmission plane and to enhance energy conduction from the energy delivery means to the tissue in order to more predictably and securely affix the closure device to the tissue. Optionally, the closure device may incorporate tissue solders or adhesives. These solders or adhesives may be designed to achieve full adhesion upon energy delivery. Conductive elements incorporated into the closure device may include conductive wires. Alternatively, conductive elements may comprise patterned doping of conductive particles into specific conductive shapes or pathways within the closure device. Example conductive wires may be made from gold, platinum, iridium, or alloys thereof. Example doping elements include powdered metals such as tantalum, platinum, gold, iridium, or alloys thereof. Example matrices include self expanding collagen, hyaluronic acid, absorbable sponge, matrices of bioabsorbable polymers, and bioresorbable metals, such as iron or nickel alloys. Example tissue solders or adhesives include autologous blood, albumin, collagen, fibrin, cyanoacrylates, mussel byssus adhesives, polymer hot melt adhesives or the like. Combinations of several of these solders or adhesives may also be utilized.

Other embodiments of closure devices incorporating conductive elements may include design features such as skirts, flanges or lips which are designed to engage the tissue of the right atrium adjacent to the PFO, acting as a positive stop and as additional retention means. In some cases, the closure device will incorporate deformable non-resorbable frame members in order to facilitate closure device positioning and retention.

BRIEF DESCRIPTION OF THE DRAWING FIGURES

DETAILED DESCRIPTION OF THE INVENTION

Methods and apparatus of the invention generally provide for treating tissue adjacent a patent foramen ovale (PFO) to cause closure of the foramen. The methods and devices typically include a catheter device which can be advanced through the vasculature of a patient to position the distal end of the catheter near the PFO to provide treatment. Treatment apparatus disposed at or near the distal end of the catheter can then be used to treat at least a portion of the heart wall tissue surrounding the PFO, to cause the PFO to close. In many embodiments, the treatment apparatus is used to transmit energy to a closure device and to the tissues surrounding the PFO. The energy causes bonding to occur between the tissue of the PFO and the closure device, which may in turn induce a response in the tissues which causes the PFO to close. In one embodiment, the treatment apparatus includes one or more conductive elements. Such conductive elements may be retractable into (and extendable out of) the body of the catheter.

In some embodiments, closure devices may be made from bioresorbable materials such as collagen, hyaluronic acids, or various formulations of bioresorbable polymers such as PLLA, PLGA, degradable metals or the like. Alternatively, closure devices may comprise one or more non-resorbable materials, such Dacron®, ePTFE, non-degradable metallic weaves such as platinum alloys, gold, nitinol or stainless steel, or composites of several of these materials. The closure device may be self expanding or expandable to fill gaps left between the tissues of the PFO after they are brought into apposition for sealing. Of particular interest are embodiments wherein conductive particles are incorporated into the matrix of the closure device to increase conductivity and inductance through the closure device and the tissues of the PFO in order to increase the efficacy and consistency of the closure. These particles may be evenly distributed throughout the matrix of the closure device, or they might be arranged into specifically designed conductive pathways.

For the purposes of this description, the tissue surrounding, encircling or forming a PFO will generally be referred to as "tissue adjacent the PFO" or "PFO tissue" or "tissue surrounding the PFO." A "PFO" itself is actually a foramen, or opening, in tissue of the heart wall between the left and right atria (the interatrial septum), while tissue adjacent the PFO is tissue of the septum primum and the septum secundum that has failed to fuse, thus leaving the foramen ovale patent. Many embodiments of the present invention involve apparatus and methods acting on tissue adjacent the PFO, and it should be emphasized that "tissue adjacent the PFO" means tissue of the septum primum, tissue of the septum secundum, and/or any other adjacent heart wall tissue upon which an embodiment of the invention may act.

Figure 1:
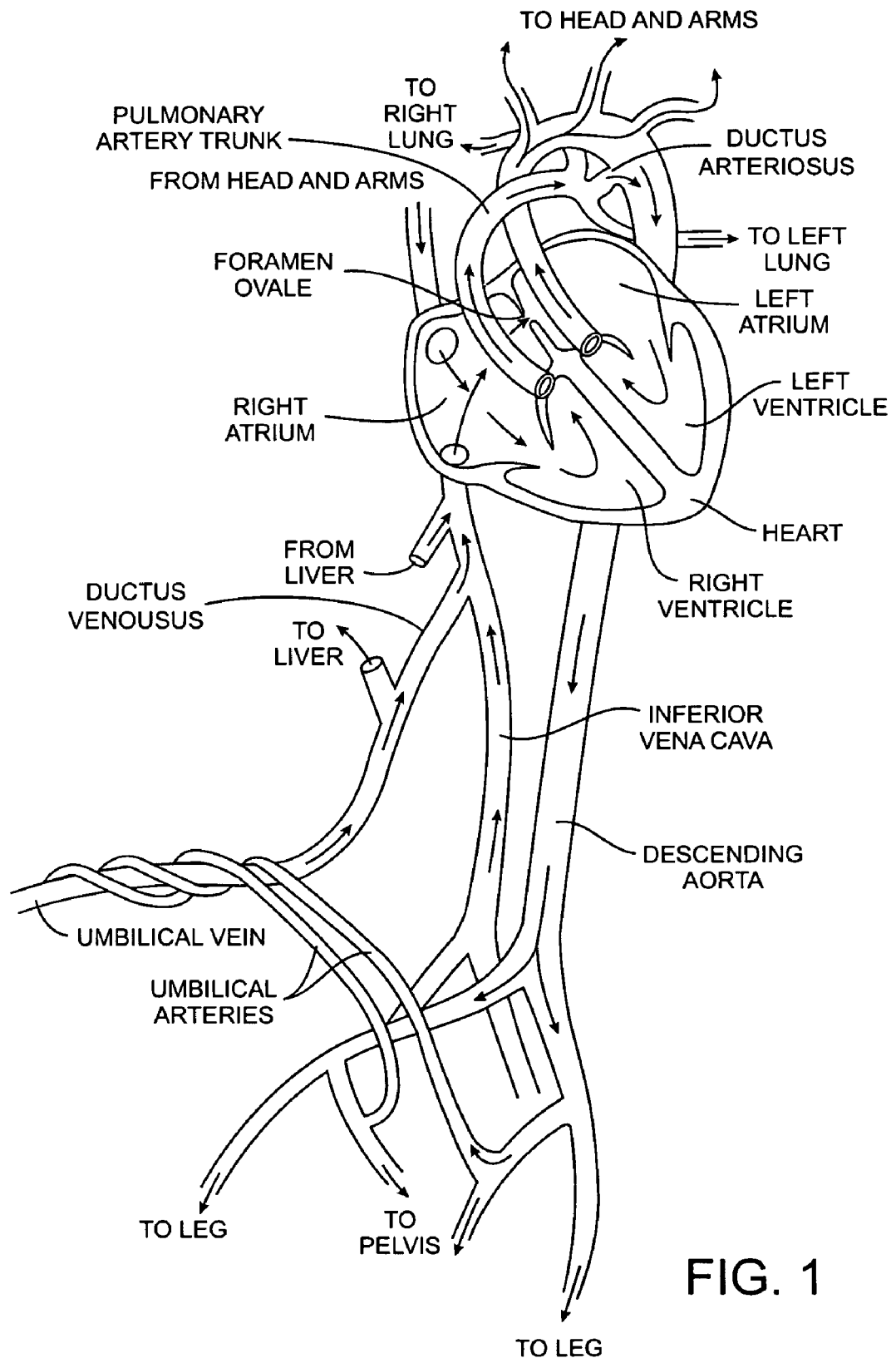
FIG. 1 is a diagram of the fetal circulation.
Figure 2:
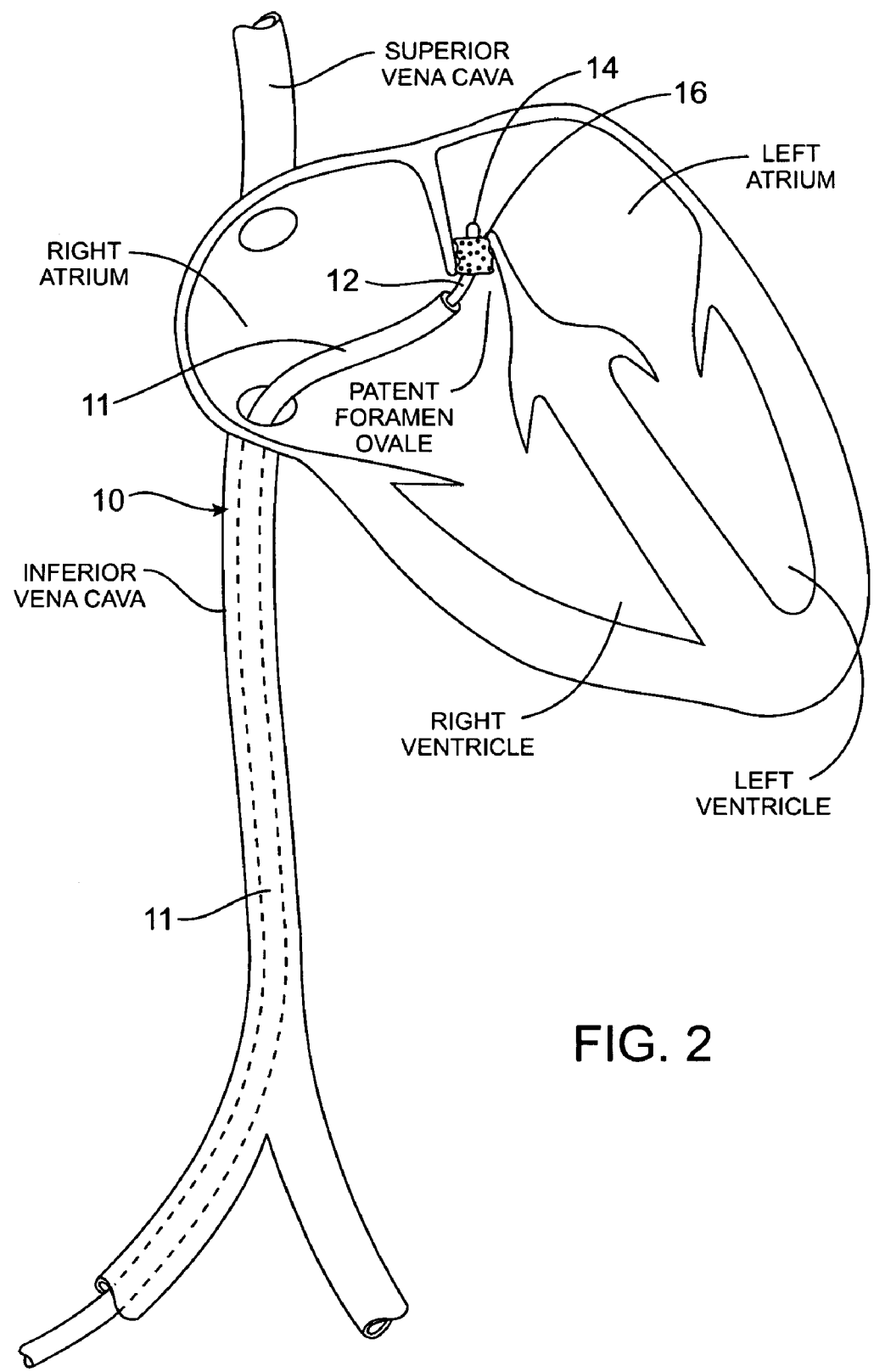
FIG. 2 is a diagram of a catheter apparatus according to an embodiment of the present invention, having a conductive element and closure device, the catheter passing through the inferior vena cava and right atrium and through the patent foramen ovale.
Figure 3A:
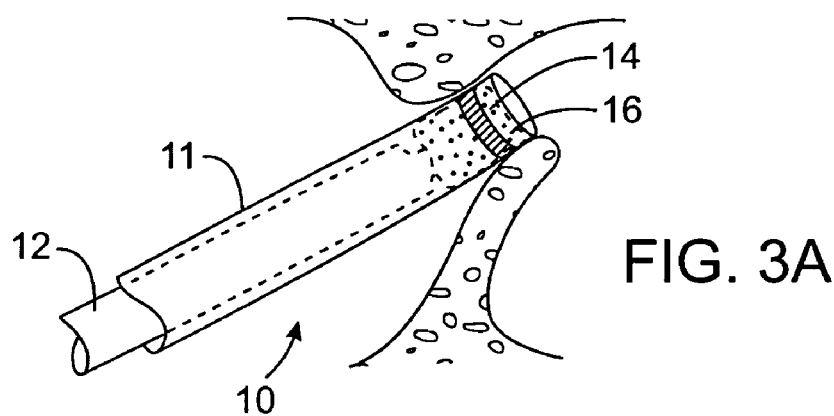
FIGS. 3A–3C are a diagram of a catheter apparatus according to an embodiment of the present invention, having a conductive element and closure device.
Figure 3B:
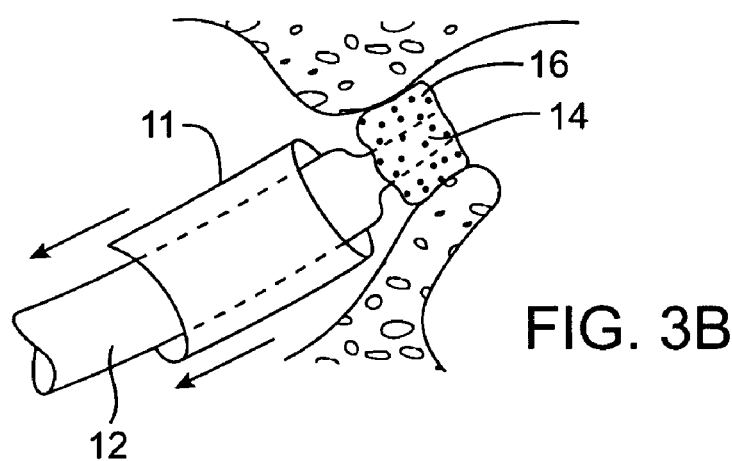
Figure 3C:
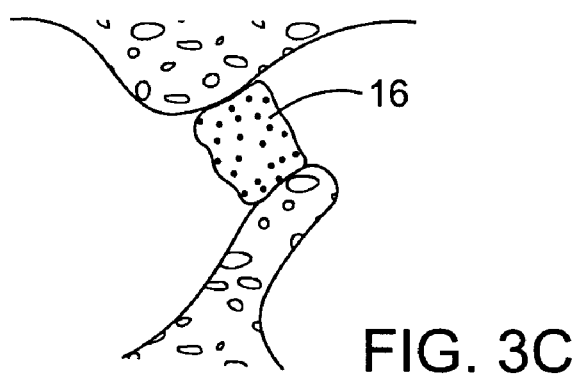

FIG. 2 shows a catheter system 10 according to an embodiment of the present invention in place across a PFO, and FIGS. 3A–3C demonstrate the use of such a catheter system 10. In one embodiment, catheter system 10 consists of an outer delivery catheter 11 and in inner catheter 12 with at least one treatment apparatus 14 and at least one closure device 16 disposed at its distal tip. Treatment apparatus 14 may comprise, for example, at least one conductive element for transmitting energy such as radiofrequency energy to the closure device and to the tissue of the PFO. Closure device 16 may be any of the embodiments discussed further below, such as a bioresorbable or non-resorbable matrix or patch, or any other device for closure of a PFO.

As shown in FIGS. 3A–3C, delivery catheter 111 is placed through or into the PFO, with inner catheter 12 having treatment apparatus 14 and closure device 16 housed within it. Outer delivery catheter 11 is withdrawn to expose treatment apparatus 14 to the tissues of the PFO. Energy is applied via treatment apparatus 14 to closure device 16 to cause closure device 16 and/or tissue solders or adhesives within the matrix of closure device 16 to bond with the tissues of the PFO, securing closure device 16 to the tissue. Optionally, closure device 16 may incorporate conductive or inductive particulate material in order to enhance energy transmission and tissue bonding. Once the bond is complete, energy delivery ceases and the entire delivery system 10 and treatment apparatus 14 are withdrawn from the body, leaving closure device 16 in place. Closure device 16 may be constructed of a sponge-like material that will self-seal upon withdrawal of the treatment apparatus from closure device 16. Optionally, treatment apparatus 14 might be withdrawn from closure device 16 as energy is being applied, sealing the track of the treatment apparatus 14 as it is withdrawn.

Devices such as those described in FIGS. 2 and 3A–C will most preferably make use of monopolar radiofrequency (RF) energy transmitted from the conductive elements of the treatment apparatus, through the patient, completing the circuit to a ground pad affixed to the external skin of the patient. Control systems within the energy delivery systems may automatically stop energy delivery upon detecting a change in condition of energy delivery, for instance an increase in electrical resistance or impedance within closure device 16 and/or tissues, or an increased energy draw from the treatment apparatus. In other embodiments, bipolar RF energy may be transmitted from the treatment apparatus. Alternatively, other forms of energy may be applied to one or more closure devices and/or to tissues adjacent a PFO, such as but not limited to resistive heating, ultrasound, microwave or laser energy.

Figure 4:
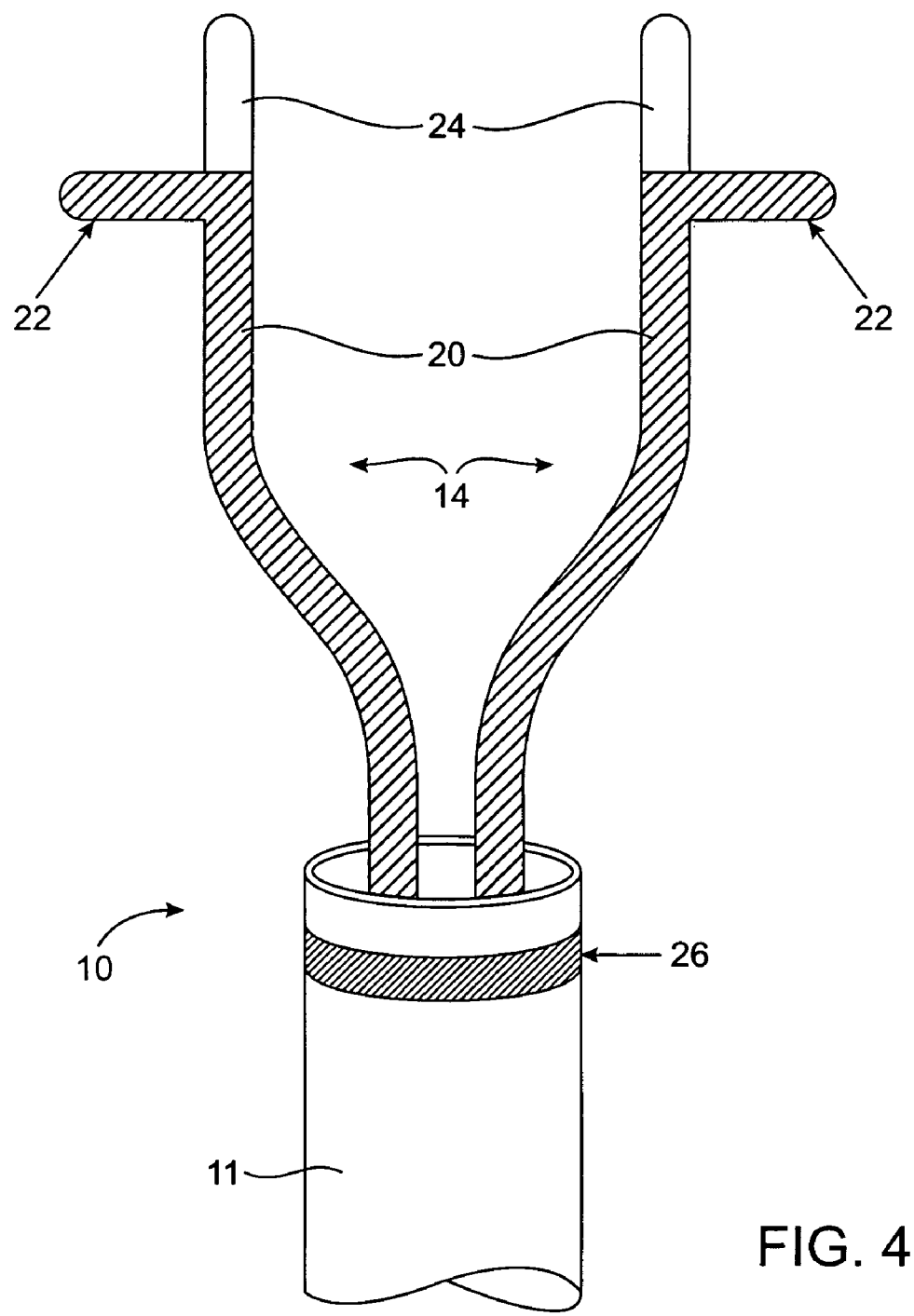
FIG. 4 is a diagram of a catheter apparatus according to an embodiment of the present invention, having multiple conductive elements and positive stops.

FIG. 4 shows a distal end of one embodiment of a catheter 10 having treatment apparatus 14 comprising two conductive elements, each having an insulated proximal portion 20, a "positive stop" 22, and an uninsulated distal energy transmission portion 24. Catheter 10 may also include a ground site 26 for bipolar use. In this embodiment, a closure device of the types described elsewhere in this disclosure may span the distance between the uninsulated energy transmission portions 24 of the conductive elements. Positive stops 22 engage the peripheral limits of the PFO in order to allow passage of treatment apparatus 14 to a predetermined depth within the PFO. The multiple conductive elements may be made to separate through spring-action or through positive mechanical means in order to apply lateral forces to the PFO, stretching the tissue of the septum primum and septum secundum and bringing the edges of these tissue structures into apposition.

Figure 5A:
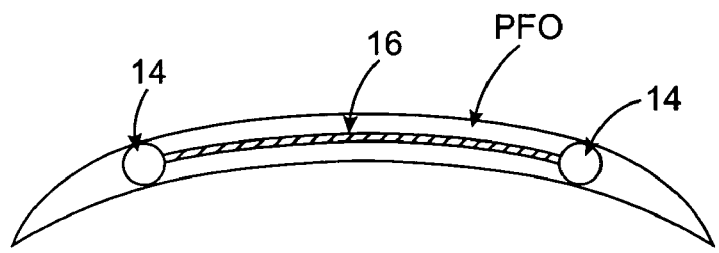
FIGS. 5A–5D are diagrams showing the delivery of devices according to an embodiment of the present invention, wherein lateral force and expanding matrices are used to close a PFO.
Figure 5B:
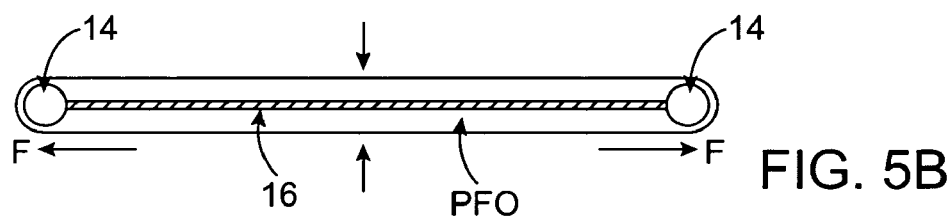
Figure 5C:
Figure 5D:
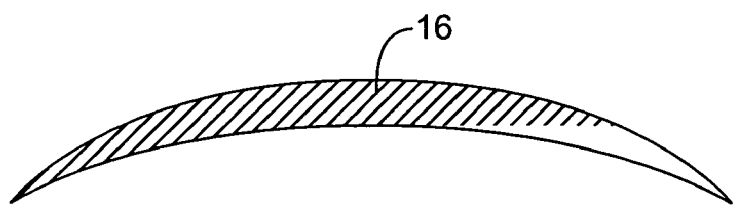
Figure 6:
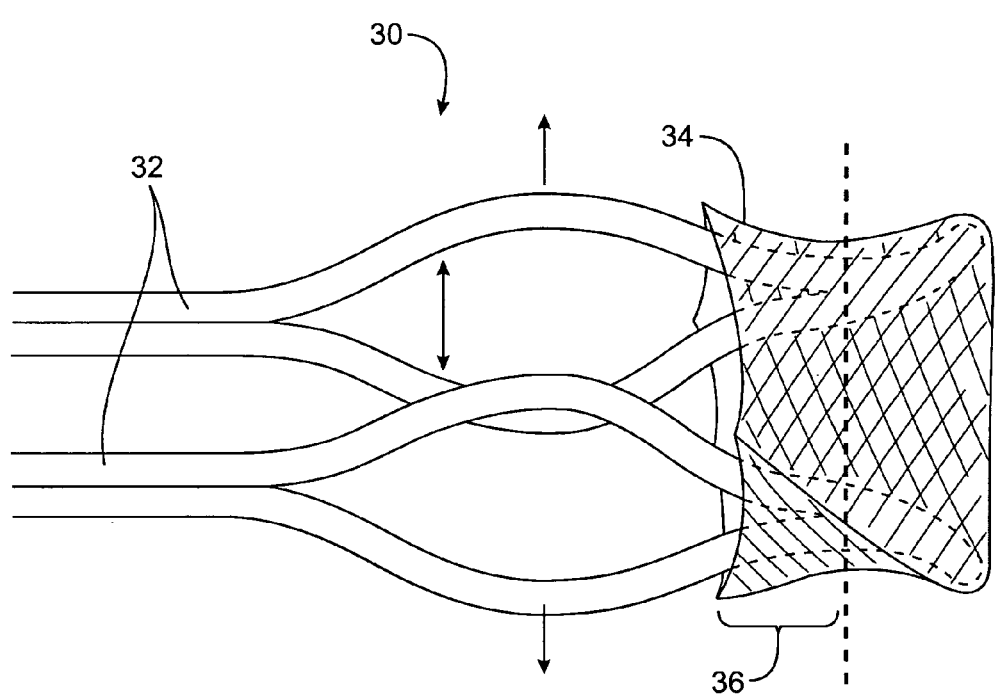
FIG. 6 is a diagram of a catheter apparatus according to an embodiment of the present invention, having multiple conductive elements which apply lateral and dilatory force to the PFO.

FIGS. 5A–5D show the use of a device such as that described in FIG. 4. The system is delivered to the PFO as previously described, and upon reaching the PFO a delivery sheath is withdrawn, exposing the treatment apparatus 14 and positive stop. The lateral motion (FIG. 5B) of the treatment apparatus 14 and the positive stops 22 assist in bringing the closure device into position within the PFO, and in bringing the tissues of the PFO in apposition to one another. Optionally, the matrix may expand to fill any voids between the tissues of the PFO (FIG. 5C). Energy is applied to the closure device via the conductive elements of the treatment apparatus 14, and the delivery system and the treatment apparatus 14 are withdrawn (FIG. 5D). Bipolar energy may be applied between the conductive elements or between the elements and the ground site 26.

Figure 7A:
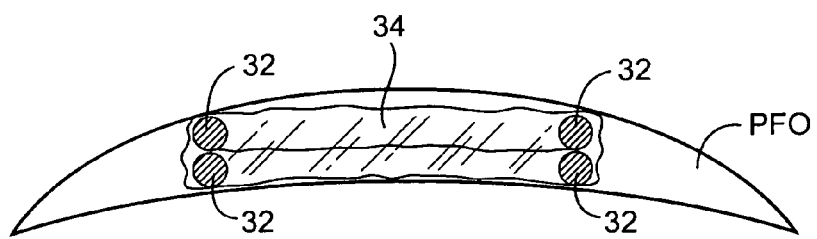
FIGS. 7A–7C are diagrams showing the delivery of devices according to an embodiment of the present invention, wherein lateral and dilatory forces and closure devices are used to close a PFO.
Figure 7B:
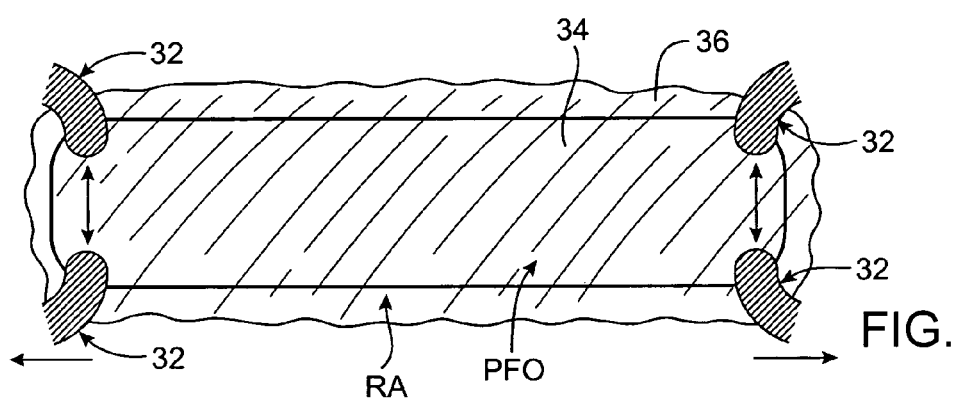
Figure 7C:
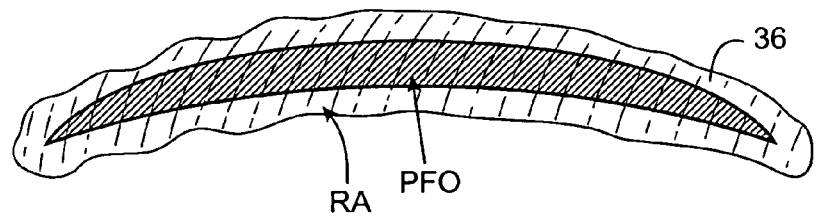

FIGS. 6 and 7A–C show a treatment apparatus 30 having multiple conductive elements 32 which apply both lateral and dilatory force to the PFO, in order to more forcefully bring a closure device 34 into apposition with the tissues of the PFO. In some embodiments, closure device 34, which may incorporate any of the features previously disclosed, may form a closed-ended sock-like structure. In some embodiments, the proximal edge of closure device 34 may be positioned on conductive elements 32 such that when lateral and dilatory forces are exerted on closure device 34 and the tissues of the PFO, the proximal portion of closure device 34 forms a skirt 36 which contacts the tissue of the right atrium peripheral to the PFO. In this embodiment, as shown in FIGS. 7B and 7C, energy application may cause a main portion of closure device 34 to adhere to the tunnel of the PFO, while the skirted area 36 adheres to the right atrial tissue surrounding the PFO tunnel.

Figure 8:
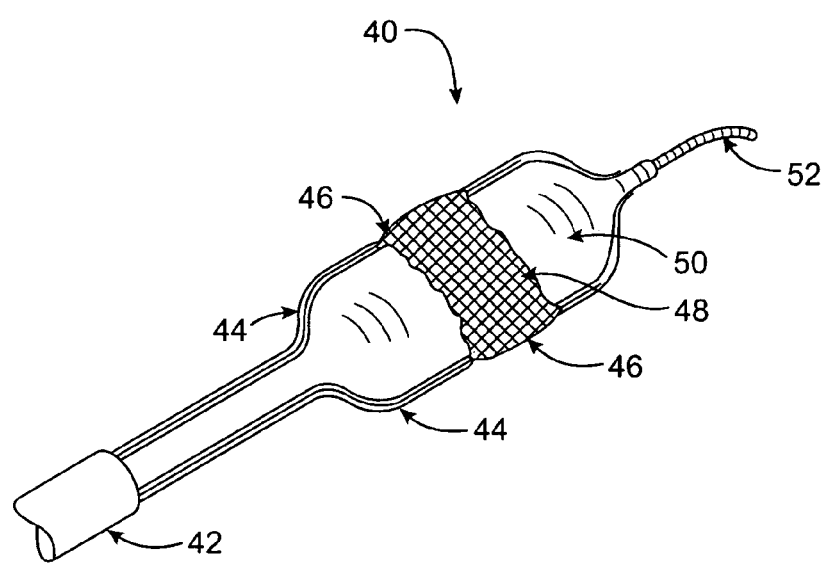
FIG. 8 is a diagram of a catheter apparatus according to an embodiment of the present invention, having multiple conductive elements which apply lateral and dilatory force to the PFO via balloon actuation.

FIG. 8 shows an alternative embodiment of a treatment apparatus 40 extended distally from a delivery catheter 42. In this embodiment, a balloon 50 exerts dilatory and lateral forces on the PFO and closure device 48. Conductive element retention wires 46 run through small lumens 44 or channels in treatment apparatus 40 and exert lateral forces on balloon 50, closure device 48 and PFO tissues, to help flatten balloon 50 and conform more closely to the natural geometry of the PFO. Retention wires 46 also act as conductive elements for delivery of energy to the closure device and PFO.

Devices such as those described in FIGS. 4, 5A–D, 6, 7A–C and 8 may make use of monopolar radiofrequency energy, wherein energy is applied simultaneously to all conductive elements, completing the circuit through an external ground pad affixed to the skin of the patient. Alternatively, bipolar energy may be applied to all conductive elements simultaneously, and the circuit completed through a ground element incorporated elsewhere on the delivery system. Further embodiments may include applying bipolar energy between two or more conductive elements of the treatment apparatus, which are electrically isolated from one another within the delivery system.

Control systems may be includes in various embodiments within the energy delivery systems for detecting and/or stopping energy delivery. Such a control system may automatically stop energy delivery upon detecting a change in a condition of energy delivery, for instance an increase in electrical resistance or impedance within the closure device and/or tissues, or an increased energy draw from the treatment apparatus. In some embodiments, a control system will stop energy delivery when a temperature is detected that relates to a sufficient temperature for tissue welding. Such control features may be accomplished by any suitable devices or combinations, such as by thermistors or the like.

Figure 9:
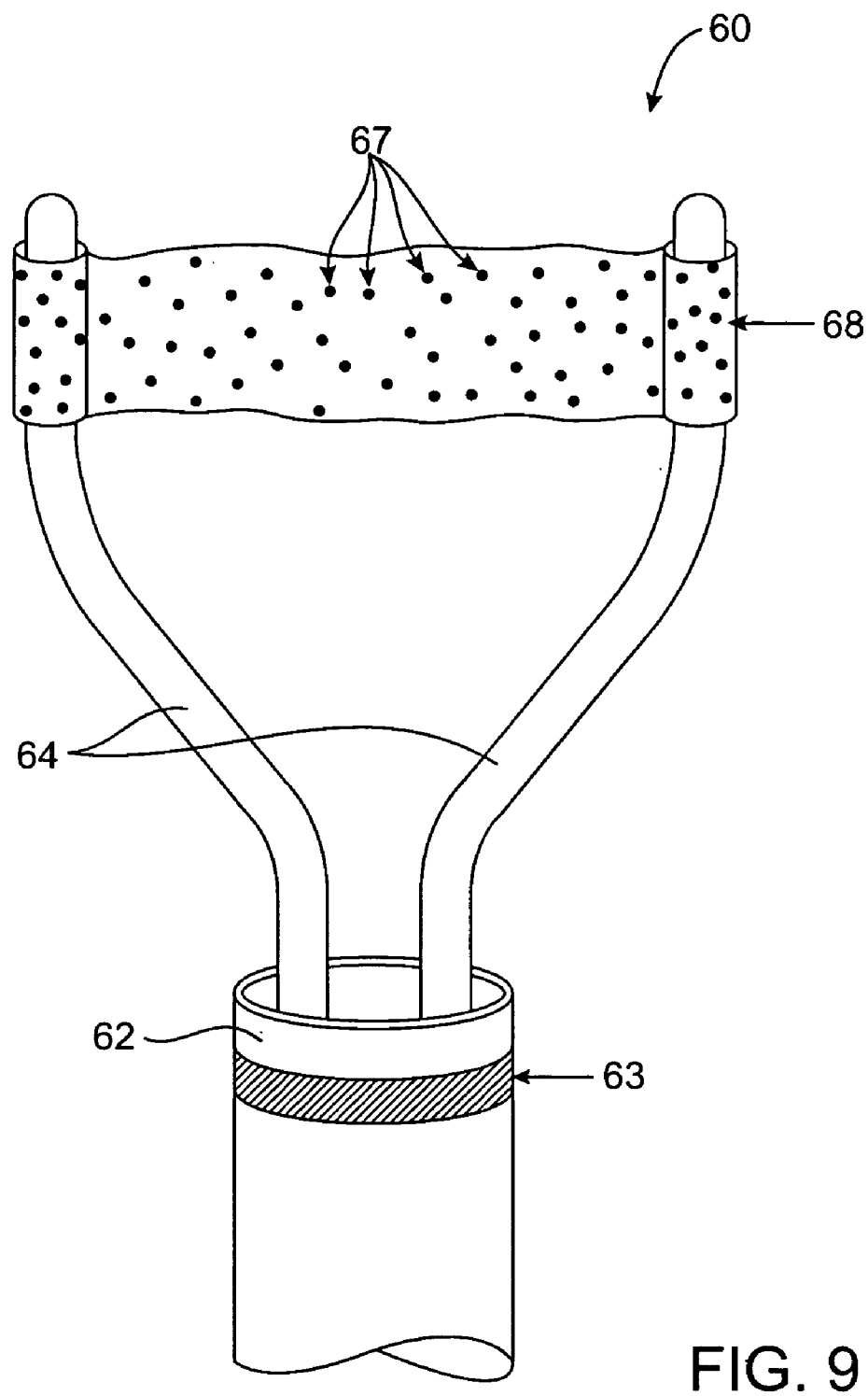
FIG. 9 is a diagram of a catheter apparatus according to an embodiment of the present invention, having multiple conductive elements and a closure device consisting of a conductively doped matrix.

FIG. 9 demonstrates another embodiment of treatment apparatus 60 extending out of a delivery catheter 62, the latter of which includes an optional electrical ground 63. In this embodiment, the closure device 68 is doped with an approximately even distribution of conductive particles 67 within a bioresorbable matrix. Conductive particles 67 may include, for example, powders of gold, platinum; steel, tantalum, tungsten, iridium, or alloys or combinations thereof. In any case, it will be desirable for the particle size to be smaller than a red blood cell (about 20 microns) so that upon resorption of the binding matrix of the closure device, individual conductive particles 67 may pass through the body for filtration and expulsion by the liver or kidneys without causing obstruction within the vascular bed. Generally, conductive particles 67 reduce impedance in the tissues adjacent the PFO and thus assist energy transmission to the tissues.

Figure 10:
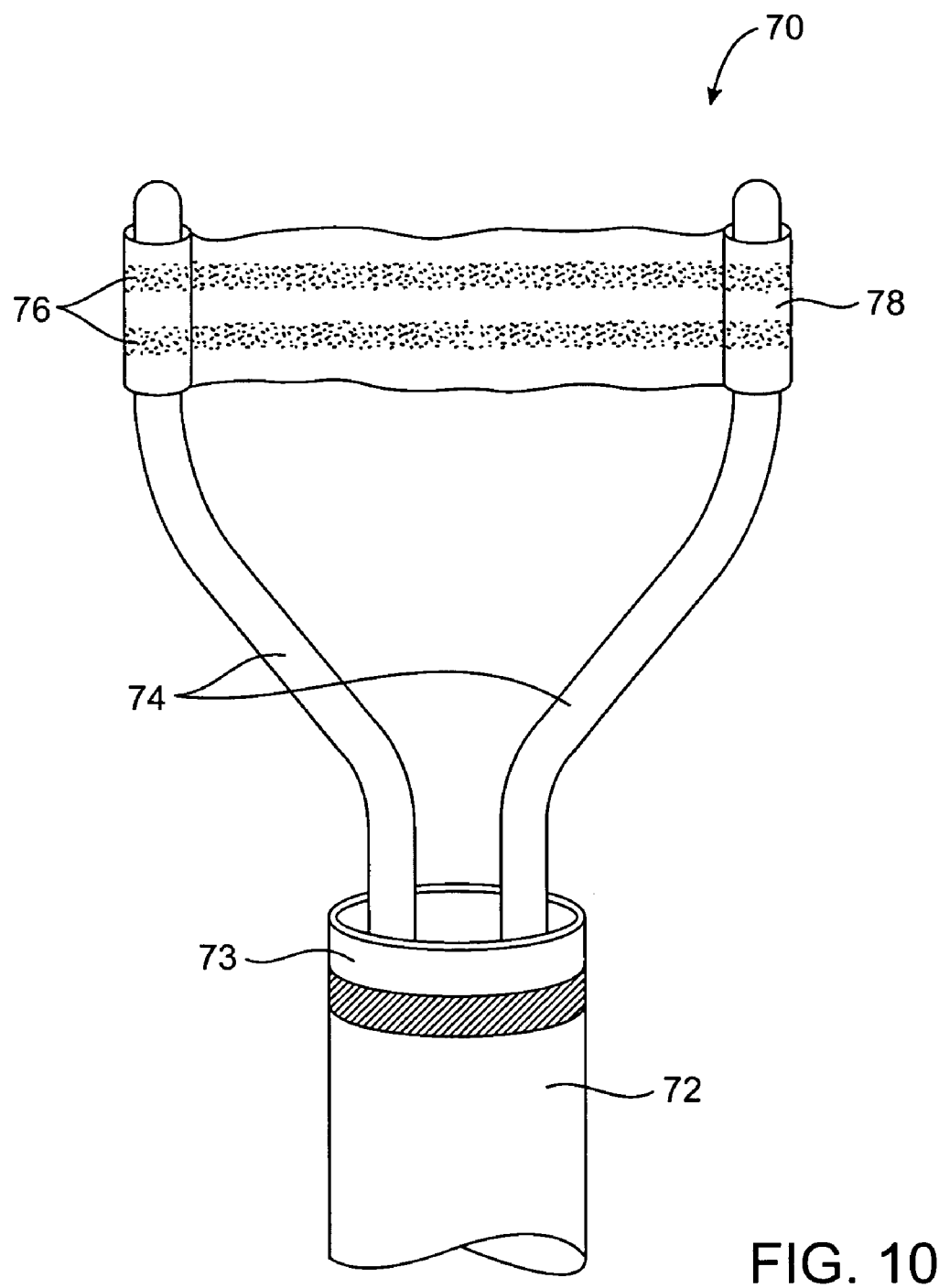
FIG. 10 is a diagram of a catheter apparatus according to an embodiment of the present invention, having multiple conductive elements and a conductive particle-doped closure device, wherein the conductive doping particles form specific conduction pathways.

FIG. 10 demonstrates another embodiment of treatment apparatus 70 extending from a delivery catheter 72 having an electrical ground 73. In this embodiment, specific patterns of doped material 76 are created on a closure device 78 by selectively doping portions of the closure device matrix 78. The doped material pattern 76 may be electrically conductive, or it may simply reduce the electrical resistance or impedance along which a signal might preferentially pass without actually being conductive. In the embodiment shown, at least one specific path is created which is in connection with both conducting elements 74 of treatment apparatus 70. This embodiment will be particularly useful in a monopolar energy delivery arrangement or with bipolar energy delivery when the return path is part of the delivery system (as with ground 73).

Figure 11:
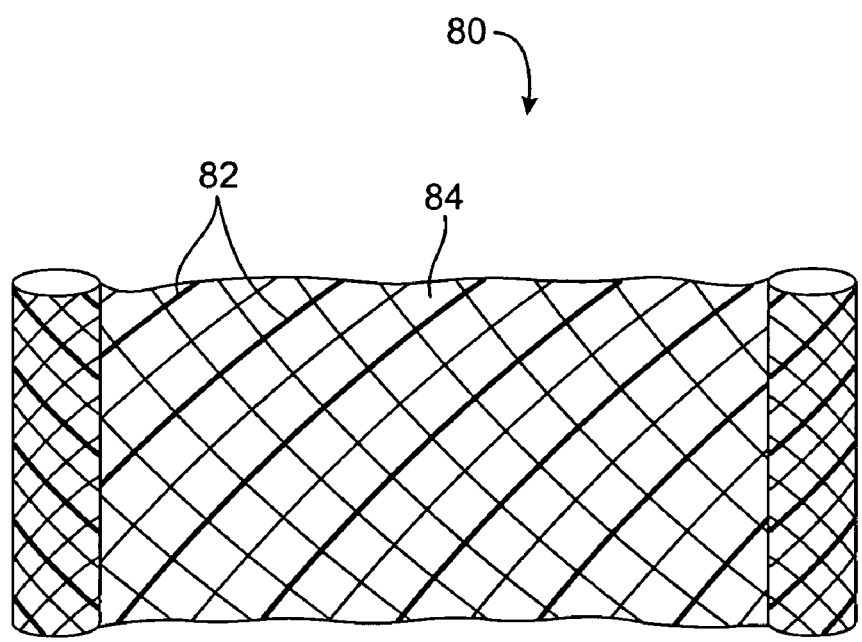
FIG. 11 is a diagram of a closure device according to an embodiment of the present invention, having conductive elements and bioresorbable elements.

FIG. 11 demonstrates an alternative embodiment for an electrically conductive or reduced resistance closure device 80 wherein a woven or braided fabric is created from alternating fibers of bioresorbable fibers 84 and electrically conductive or reduced resistance fibers 82. In this embodiment, the electrically conductive or reduced resistance/impedance fibers 82 will be metal fibers, rather than pathways created from selective doping of particles. Any electrically conductive or reduced resistance/impedance wire material will be suitable for the application, such as gold, steel, platinum, copper, a resorbable metal such as an iron or nickel alloy, or the like. This closure device can be made to work with either bipolar or monopolar energy delivery, depending on the exact scheme of coupling of the conductive fibers 82 to the conductive elements of the treatment apparatus.

Figure 12:
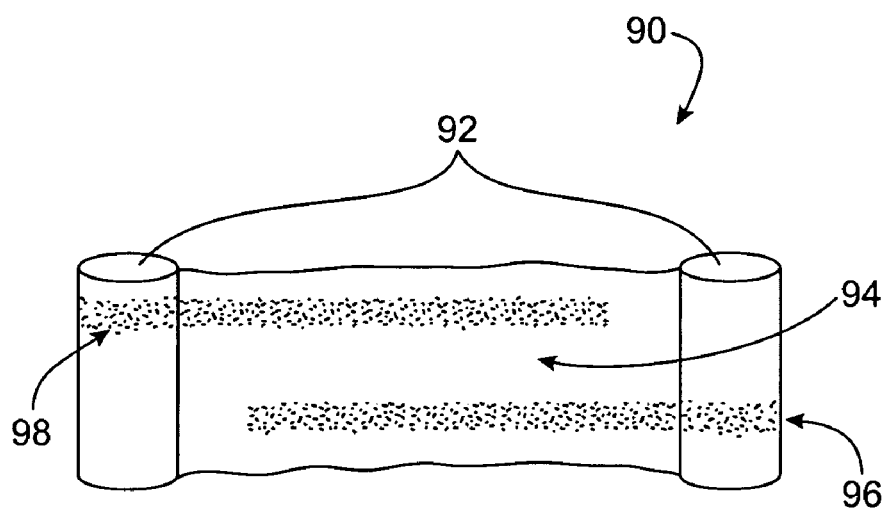
FIG. 12 is a diagram of a catheter apparatus according to an embodiment of the present invention, having multiple conductive elements and a conductive particle-doped closure device wherein the conductive doping particles form specific conduction pathways which are electrically isolated from one another.

FIG. 12 shows yet another embodiment of a closure device 90, having attachment elements 92 for removably coupling closure device with conductive elements of treatment apparatus, one or more insulation zones 94 and two or more selectively doped conductive or reduced resistance or impedance pathways 96, 98. In this embodiment, pathways 96, 98 are arranged so that at least a first pathway 96 is most closely coupled with one conduction element of the treatment apparatus, and at least a second pathway 98 is most closely coupled with another conduction element of the treatment apparatus, with one or more insulation zones 94 disposed between pathways 96, 98. This embodiment is particularly suited for bipolar energy transmission.

Figure 13:
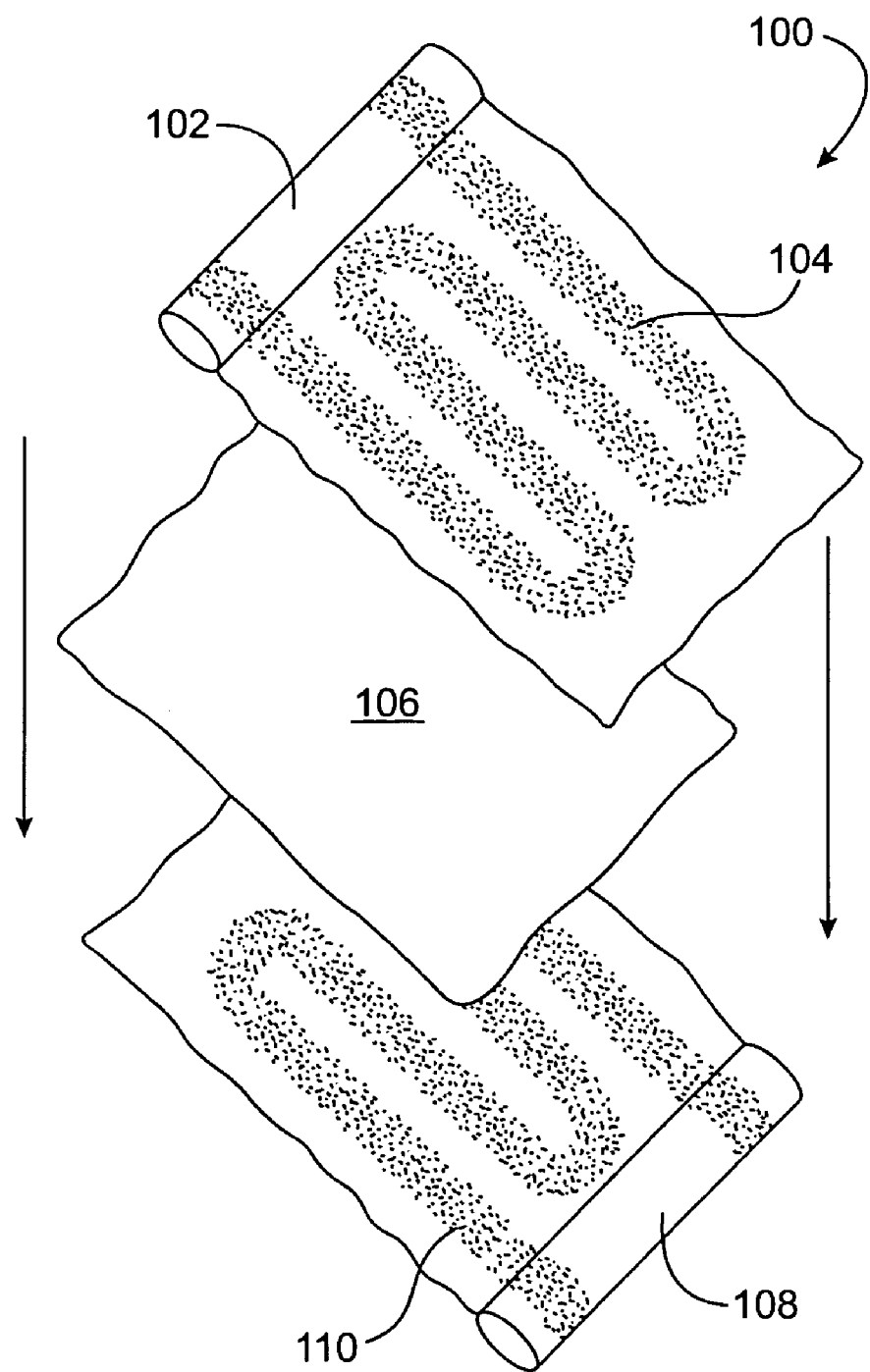
FIG. 13 is a diagram of a catheter apparatus according to an embodiment of the present invention, having multiple conductive elements and a conductive particle-doped closure device, wherein the conductive doping particles form specific conduction pathways which are electrically isolated from one another in a multi-layer configuration.

FIG. 13 demonstrates a variation of the multiple-pathway arrangement of FIG. 12. In this embodiment, a closure device 100 includes an upper conductive layer 102 having at least a first pathway 104, a middle layer 106 providing insulation, and a lower conductive layer 108 having at least a second pathway 110. The layers are joined to form a composite closure device 100 particularly suited for delivery of bipolar energy. Alternatively, upper layer 102 may be uniformly doped to provide conductivity or reduced resistance/impedance with a first electrode, and lower layer 108 may be uniformly doped and most closely coupled with a second electrode, with middle layer 106 again providing electrical isolation.

In all embodiments describing doping of a matrix to enhance energy transfer, association of a given doped pathway, whether is it highly selective to mimic a wire-like pathway or uniformly distributed to form a plate-like plane, the pathway may be made to be in true electrical connection with its intended conduction element, or it may simply be more strongly coupled with a given electrode than with a different electrode. True electrical conductivity may be established through the pathway or plane, or the mechanism of increased energy transfer may be that of reducing the impedance of a given path which it is desired for the energy to follow.

As is mentioned above, closure devices of the present invention may be entirely bioresorbable, partially bioresorbable, or entirely non-resorbable. Many of the embodiments described above are intended to be biorespoorbable but may also be constructed from non-resorbable materials. The descriptions that follow often focus on "patches" for closing a PFO. Typically, these patches will be non-resorbable, but again, bioresorbable or partially resorbable patches are contemplated. Furthermore, a "patch" may comprise any of a number of different closure devices, and therefore, the term patch should not be interpreted to limit the scope of the invention to any one embodiment or configuration. For the purposes of this application, "patch", "closure device" and the like may be used interchangeably to mean any device for closing a PFO.

Figure 14:
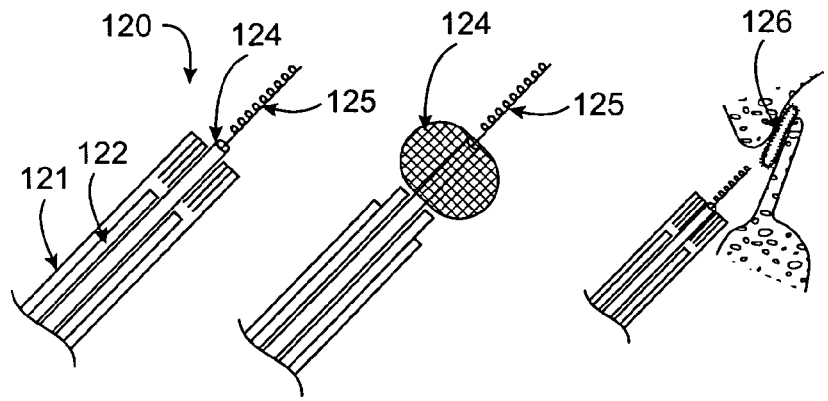
FIG. 14 is a diagram of a catheter apparatus according to an embodiment of the present invention, having a self-expanding, non-resorbable patch closure device.
Figure 15:
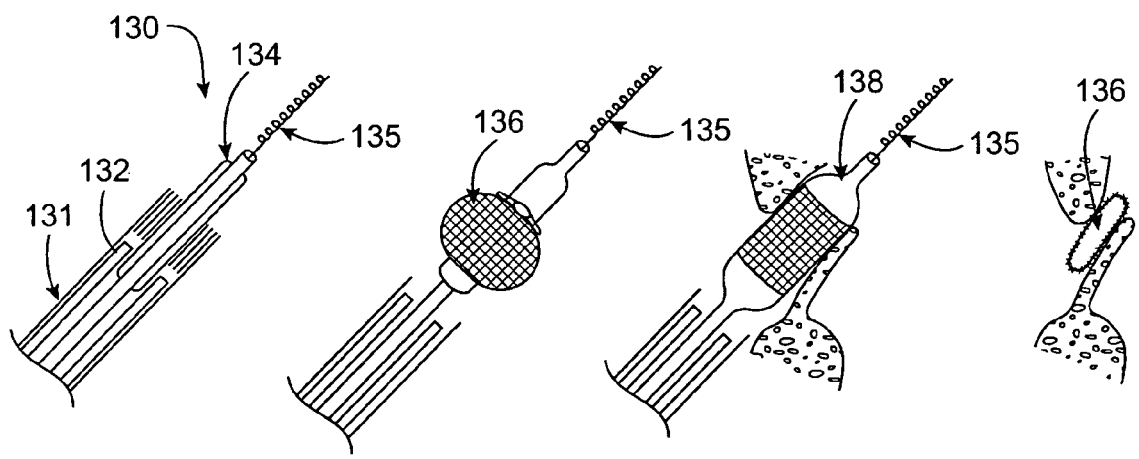
FIG. 15 is a diagram of a catheter apparatus according to an embodiment of the present invention, having a balloon-expandable, non-resorbable patch closure device.
Figure 16:
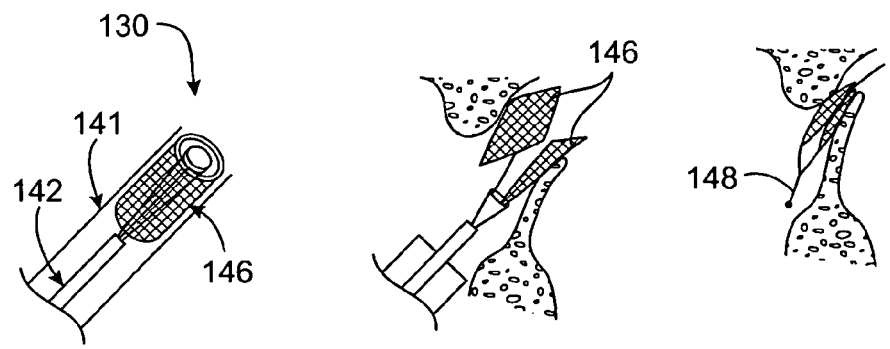
FIG. 16 is a diagram of a catheter apparatus according to an embodiment of the present invention, having non-resorbable patch members and a non-resorbable frame.

That being said, FIGS. 14, 15 and 16 illustrate apparatus and methods for welding patches using variations of normally-closed devices that are inserted into the PFO, expanded to provide secure contact to both sides of the PFO, and welded into place using energy. The device is then allowed to collapse back to its unexpanded state, sealing the PFO. Optionally, the device may be actively closed through a mechanical locking mechanism built into the device. Energy can be RF, ultrasound, microwave, resistive heating, laser, or any source that causes the device to become irreversibly adhered to the walls of the PFO. These devices may be made from a degradable metal or metal/fabric combination, so that after facilitating healing and permanent closure for the PFO, the device degrades and disappears. The devices optionally include a non-degradable fabric patch or fitted covering which heals into the surrounding tissue prior to degradation, and serves as a permanent reinforcement and an emboli containment mechanism to prevent embolism in the event that the device erode unevenly. Implantation of such self-closing devices can be facilitated by the introduction of protein solders during the welding step to facilitate adhesion and closure. In the case where laser energy is used in conjunction with protein solder, it may be desirable to mix a dye such as indocyanine green into the solder to help increase the specificity of the laser activation to the solder site.

FIG. 14 shows deployment of a self-expanding patch 126 from a catheter device 120 having a delivery catheter 121, an inner catheter 122 and treatment apparatus 124 including a patch 126 and a conductive element 125. Patch 126 expands upon being exposed from delivery catheter 121 and is welded, using conductive element 125 to tissue adjacent the PFO to close the PFO. FIG. 15 shows a similar catheter device 130, having an outer catheter 131, an inner catheter 132, and treatment apparatus 134 including a balloon expandable patch 136, a conductive element 135 and an inflatable balloon 138. Here, patch 136 is expanded into place via balloon 138 and then welded to PFO tissues to close the PFO. FIG. 16 shows another embodiment of a catheter device 140, this embodiment including an outer catheter 141, an inner catheter 142, one or more patches 146 and a reinforcement member 148 for helping to hold patches 146 in place within the PFO.

FIGS. 17–22 illustrate devices which cover the slit-like opening of the PFO like a bike tire patch, bridging from the septum primum to the septum secundum to effect the seal. Embodiments include expanding fork-like devices, braided devices which are compressed into disciform patches, and balloon expanded patches. They can be made from traditional graft and patch materials such as Dacron® or ePTFE, from non-degradable metallic weaves such as platinum alloys, gold, nitinol or stainless steel, degradable metallic weaves such as iron or magnesium alloys, degradable polymers such as PLLA, or composites of several of these materials. Adherence can be facilitated by the active introduction during welding or prior impregnation of protein solders into the devices. All energy modalities described above can be used. These devices generally employ a second catheter element which is deployed through the PFO into the left atrium.

Figure 17A:
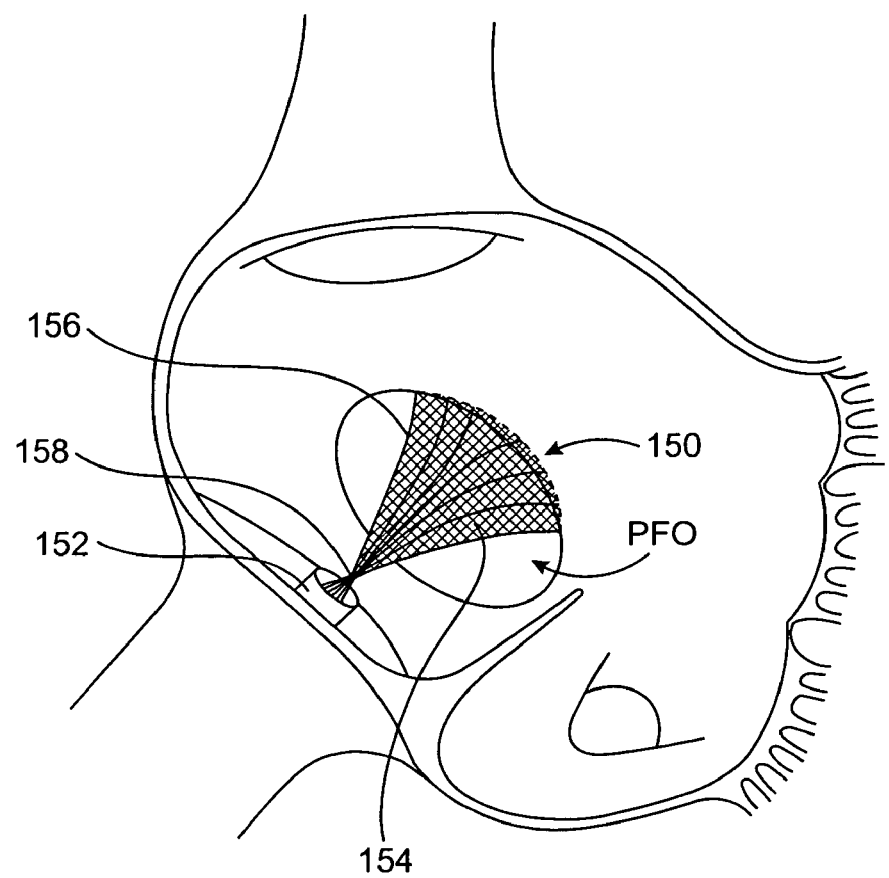
FIG. 17A is a diagram of a catheter apparatus according to an embodiment of the present invention, in position to weld a patch to tissues to close a PFO.
Figure 17B:
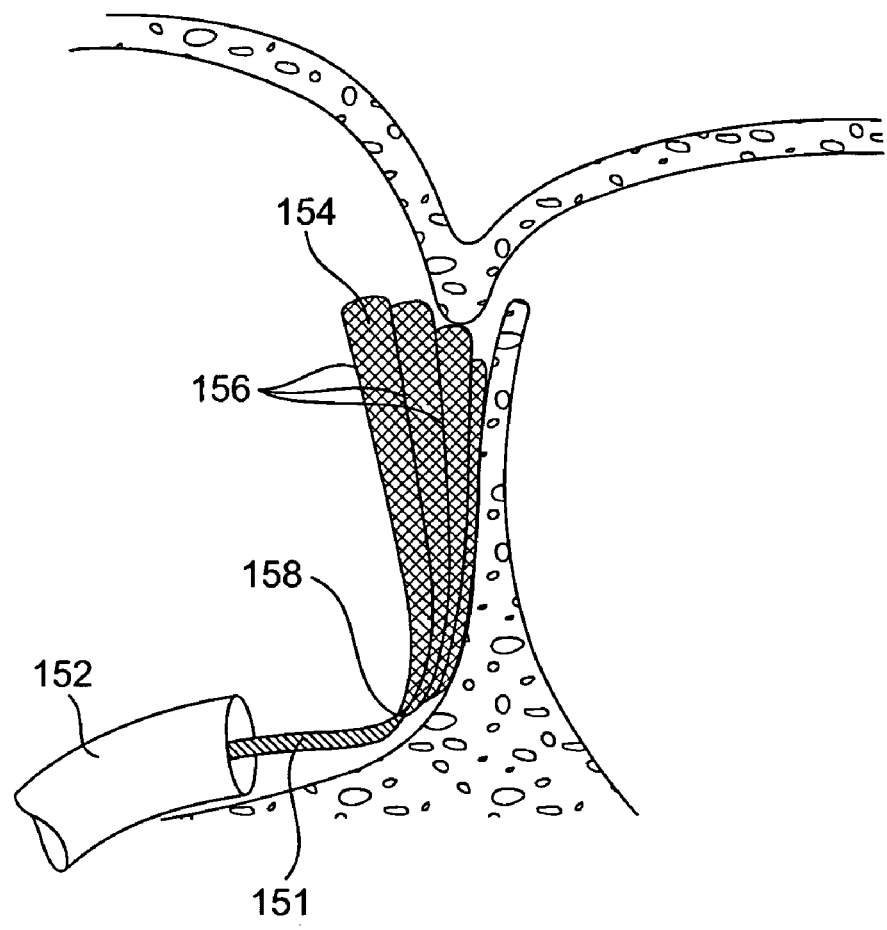
FIG. 17B is a diagram of a delivery catheter and patch according to an embodiment of the present invention.
Figure 18A:
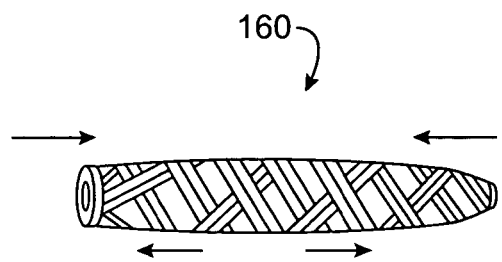
FIGS. 18A and 18B are diagrams of a PFO patch according to an embodiment of the present invention.
Figure 18B:
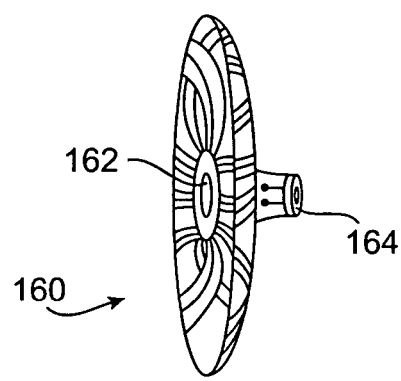
Figure 19:
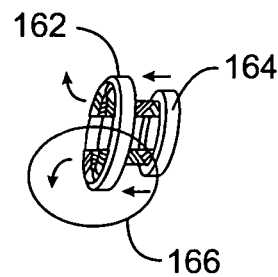
FIG. 19 is a diagram of a locking PFO patch according to an embodiment of the present invention.

FIGS. 17A and 17B show right atrial cutaway and septum cross-sectional views, respectively, of one embodiment of a tissue-welded patch device for sealing a PFO. In this embodiment, a patch 150 includes conducting fibers 156 for conducting energy and a covering mesh 154 coupled with fibers 156. Patch 150 is generally delivered by advancing through a delivery catheter 152 via an introducer rod 151. Conducting fibers 156 are coupled to an electrolytic joint 158 for transmission of energy to the wires. Upon delivery and placement, a portion of patch 150 tucks into the overlap of the septum secundum and the septum primum.

Figure 20:
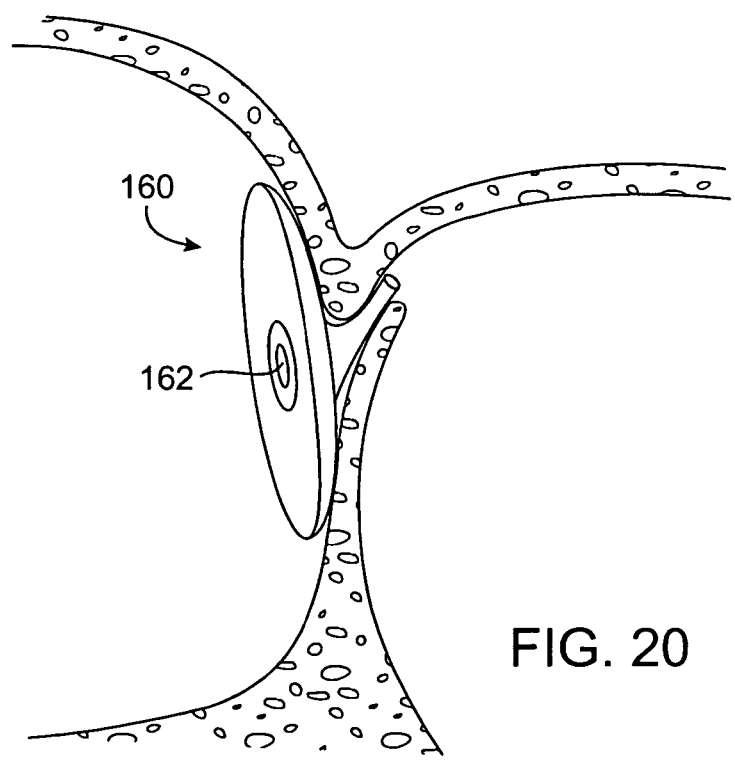
FIG. 20 is a diagram of a PFO patch according to an embodiment of the present invention in position across a PFO.

FIGS. 18A, 18B, 19 and 20 show a mushrooming patch 160 for closing a PFO. Patch 160 includes a proximal locking component 162 and a distal locking component 164 for enabling patch 160 to change from a straight configuration (FIG. 18A) for delivery to an expanded configuration (FIG. 18B) for closing the PFO. Proximal and distal locking components 162, 164 may be coupled via a snap-fit mechanism for keeping patch 160 in a mushroom-like, expanded shape. FIG. 20 shows the mushrooming patch 160 in place within the PFO.

Figure 21A:
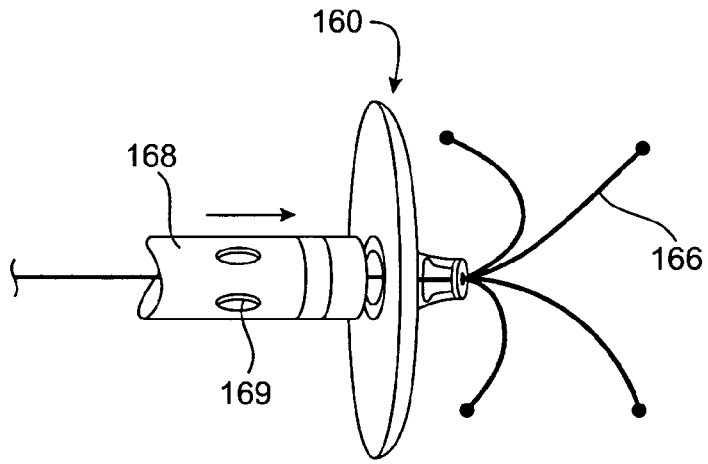
FIGS. 21A–21C are diagrams of a catheter apparatus according to an embodiment of the present invention, having a backstop member for positioning a patch in a PFO.
Figure 21B:
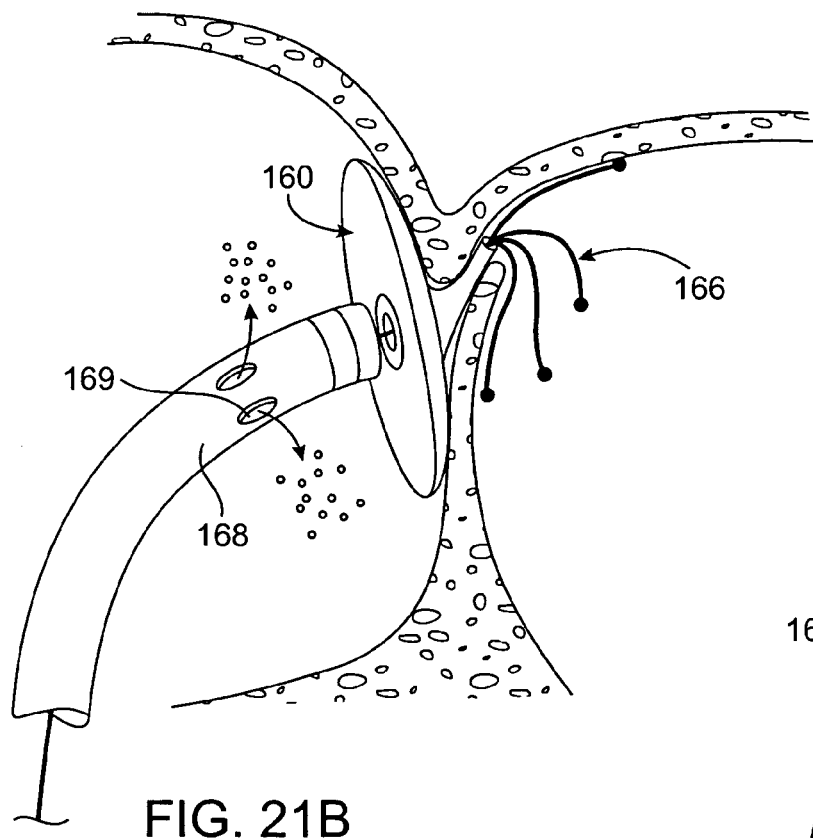
Figure 21C:
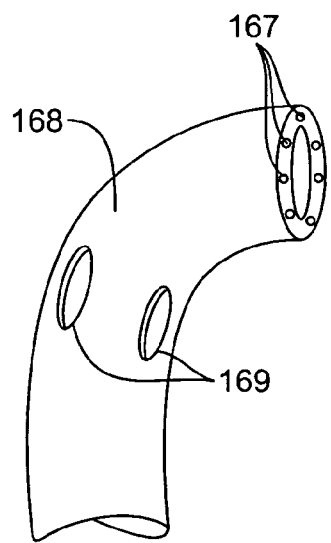
Figure 22A:
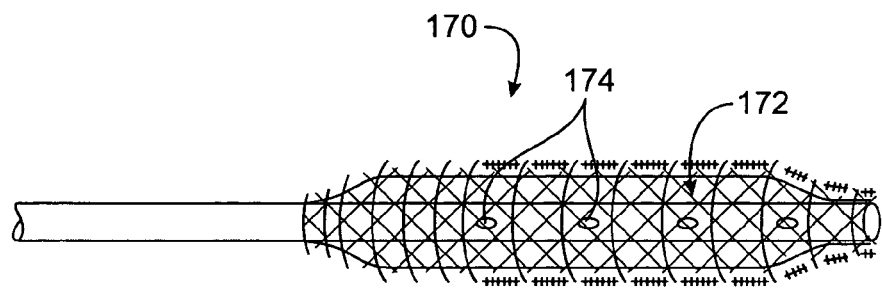
FIGS. 22A and 22B are diagrams of a catheter apparatus according to an embodiment of the present invention, having an expandable PFO patch and a backstop member.
Figure 22B:
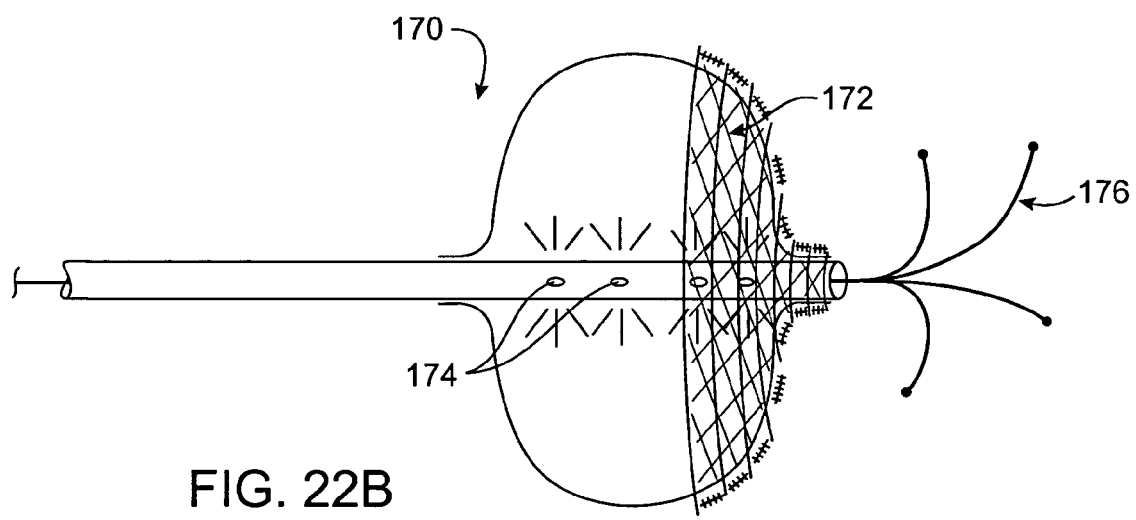

With reference now to FIGS. 21A–21C, a mushrooming patch 160 as just described may be delivered using a delivery catheter 168 having one or more infusion ports 169 for infusing a fluid such as saline. As will be described further below, a catheter system for closing a PFO may also include a backstop member 166 for helping position the patch 160 or other closure device by engaging the left atrial wall. Infusion ports 169 provide enhanced visualization of the patch placement, as the infused fluid can be visualized via an external visualization device. Alternatively, delivery catheter 168 may also include one or more visualization devices such as fiber optic fibers 167 for viewing infused fluid bubbles and/or the device delivery site directly. FIGS. 22A and 22B show a similar patch delivery device 170, having infusion ports 174 and a backstop 176, but with a balloon-expandable patch 172.

Referring now to FIGS. 22–26, in some embodiments an element of the delivery system expands in the left atrium, and serves as a backstop to help position the patch and patch delivery devices relative to the PFO. The backstop devices are removed after the patch has been deployed. Backstop devices can be balloons, wires that reform into flat coils or star-shaped elements upon deployment into the left atrium, multi-armed devices whose arms deploy radially in the left atrium and collapse back down for removal, and/or the like. In FIGS. 22–26, the backstop elements are shown without the patch or other closure device for clarity.

Figure 23:
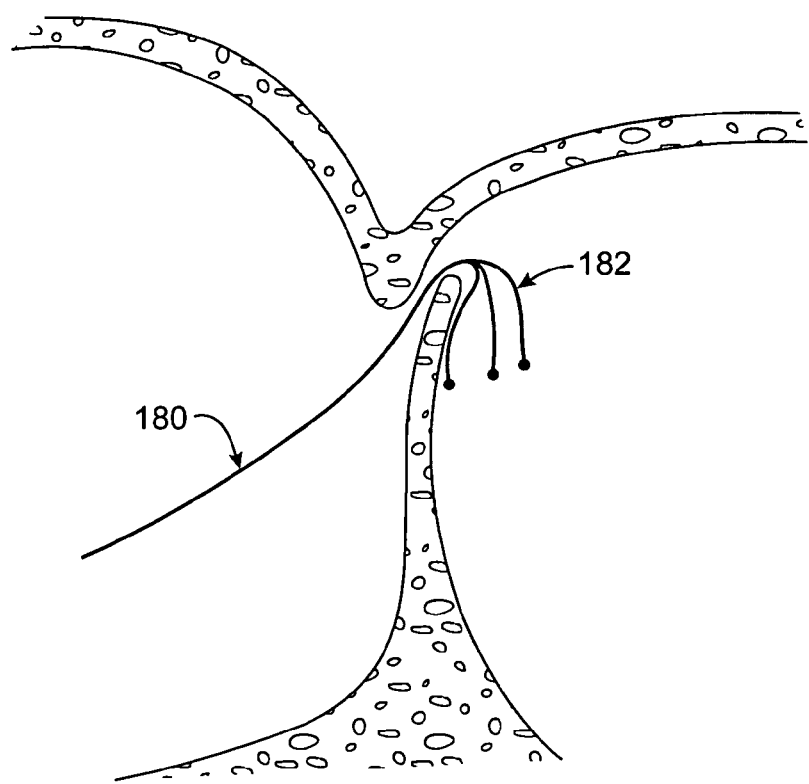
FIGS. 23–26 are diagrams of various backstop members for use in catheter apparatus according to various embodiments of the present invention.
Figure 24:
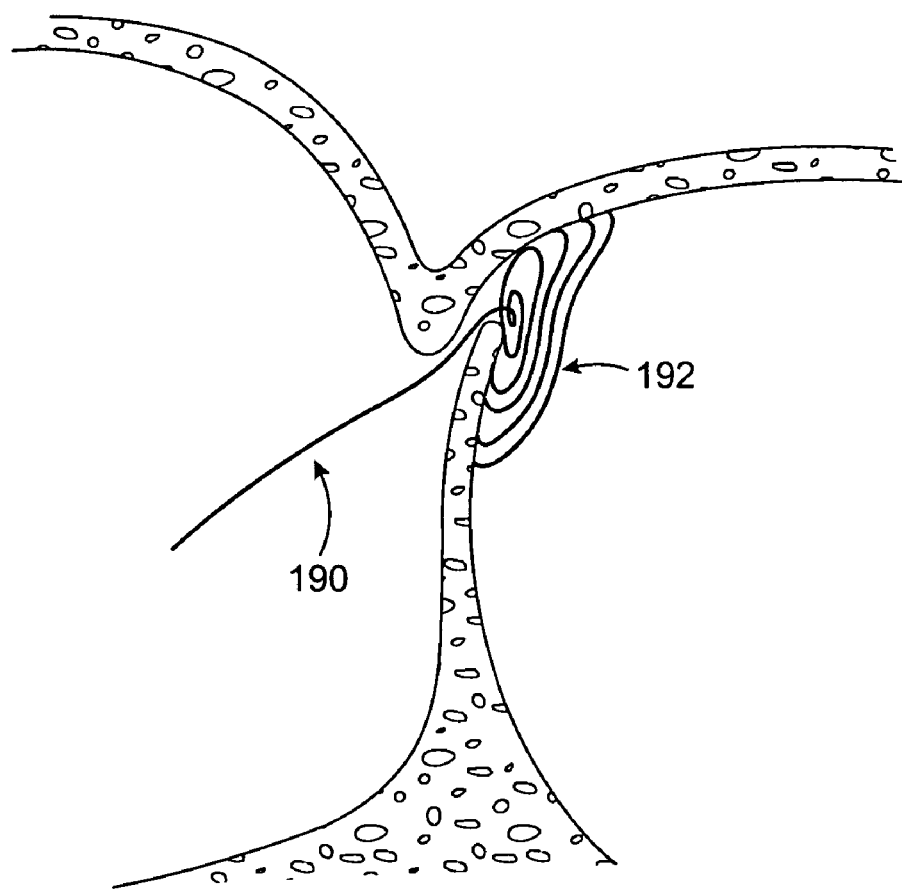
Figure 25:
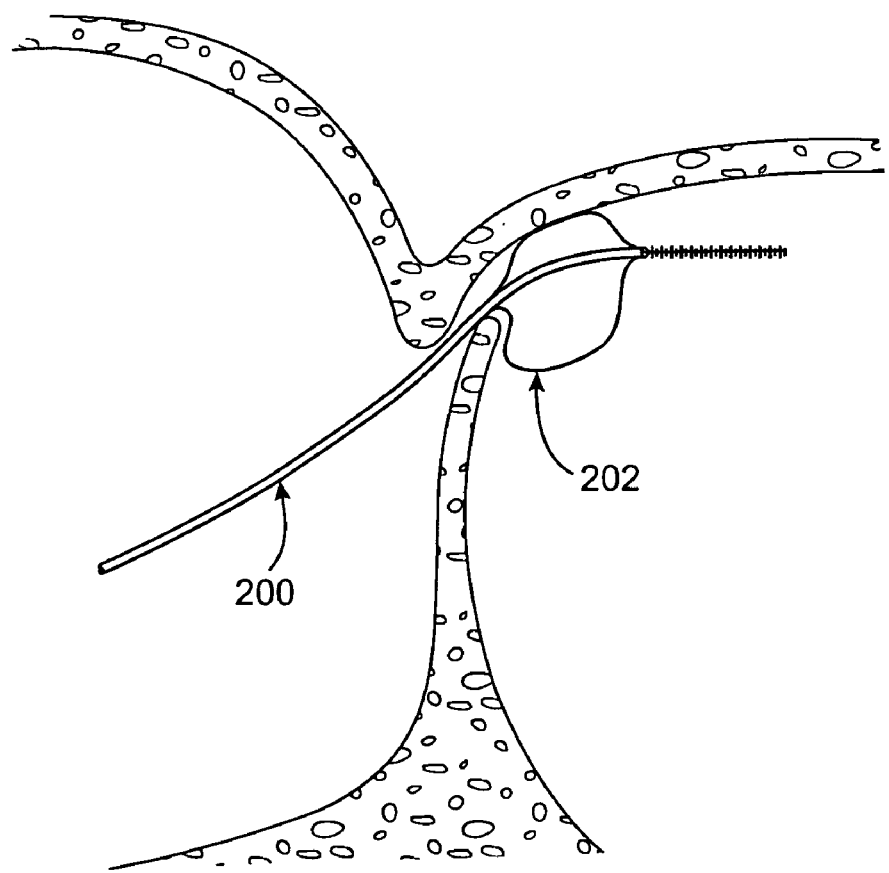
Figure 26:
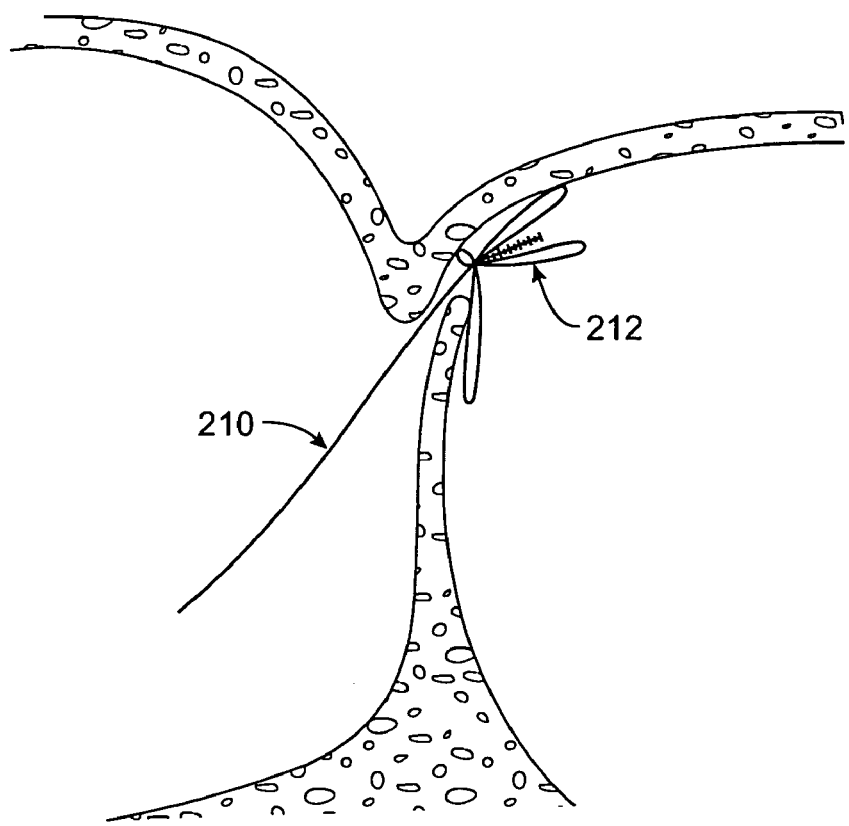

FIG. 23 shows a backstop device 180 having multiple prongs 182 that are biased inferiorly to preferentially engage the septum primum without interfering with the left atrial wall. FIG. 24 demonstrates another embodiment of a backstop device 190 having a coil 192, such as a shape memory coil that acts as the backstop. In another embodiment, as shown in FIG. 25, a backstop device 200 may use an expandable balloon 202 as a backstop member. FIG. 26 shows another backstop device 210 including a petal backstop member 212. Any of these embodiments may have a shape-changing mechanism to allow them to be delivered in a predominantly straight configuration, such as through a delivery catheter, and then expand or otherwise change shape to conform to the atrial side of the septum priumum and/or the septum secundum. Shape-changing may be accomplished by any suitable technique, such as using shape-memory materials like nitinol or spring stainless steel, inflating an expandable balloon, or the like. Once a backstop is in place, in some embodiments its shape may be locked to maintain the shape. When the patch or other closure device has been delivered to the PFO, the backstop is withdrawn, typically by restoring the backstop member to the straight configuration and withdrawing it through a delivery catheter.

Although the foregoing description is complete and accurate, it has described only a few embodiments of the invention. Various changes, additions, deletions and the like may be made to one or more embodiments of the invention without departing from the scope of the invention. Additionally, different elements of the invention could be combined to achieve any of the effects described above. Thus, the description above is provided for exemplary purposes only and should not be interpreted to limit the scope of the invention as set forth in the following claims.

What is claimed is:

1. A method of treating a patent foramen ovale, the method comprising:
   advancing a closure device near a distal end of a catheter device to tissue of the patent foramen ovale; and
   applying energy to the closure device to cause adhesion between the closure device and tissue of the patent foramen ovale, thereby fixing die closure device to tissue of the patent foramen ovale.

2. A method as in claim 1, wherein bipolar radiofrequency energy is used to cause adhesion of the closure device to the tissue.

3. A method as in claim 1, wherein monopolar radiofrequency energy is used to cause adhesion of the closure device to the tissue.

4. A method as is claim 1, wherein applying energy to the closure device comprises applying energy to at least one bioresorbable element.

5. A method as is claim 1, wherein applying energy to the closure device comprises applying energy to at least one non-resorbable element.

6. A method as in claim 5, wherein the energy is applied to a closure device comprising at least one of a tissue adhesive and a tissue solder.

7. A method as in claim 1, wherein the closure device is advanced such that no part of the closure device extends into the left atrium.

8. A method as in claim 1, further comprising applying lateral force to the patent foramen ovale with the closure device.

9. A method as in claim 8, further comprising applying dilatory force to the patent foramen ovale during closure.

10. A method as in claim 1, wherein the energy is applied via at least one energy transmission member disposed near the distal end of the catheter.

11. A method as in claim 1, wherein applying energy comprises applying resistive heating, ultrasound, microwave or laser energy.

12. A method as in claim 1, wherein the energy is applied through a conductive or low-resistance plane of the closure device.

13. A method as in claim 5, further including expanding an expandable balloon member near the distal end of the catheter to deploy the closure device to tissue of the patent foramen ovale.

14. A method as in claim 1, wherein the closure device is advanced into the tunnel of a patent foramen ovale.

* * * * *